US011857409B2

(12) United States Patent
Chacón Quirós et al.

(10) Patent No.: US 11,857,409 B2
(45) Date of Patent: Jan. 2, 2024

(54) MEDICAL IMPLANTS AND METHODS OF PREPARATION THEREOF

(71) Applicant: Establishment Labs S.A., Alajuela (CR)

(72) Inventors: Juan José Chacón Quirós, Alajuela (CR); Roberto De Mezerville, Alajuela (CR); John Hancock, Santa Barbara, CA (US); Salvador Dada, Alajuela (CR); Nathalia Araujo, Alajuela (CR); Josue Cascante, Alajuela (CR); Rudy A. Mazzocchi, New York, NY (US)

(73) Assignee: Establishment Labs Holdings, Inc., Alajuela (CR)

( * ) Notice: Subject to any disclaimer, the term of this patent is extended or adjusted under 35 U.S.C. 154(b) by 384 days.

(21) Appl. No.: 17/326,493

(22) Filed: May 21, 2021

(65) Prior Publication Data
US 2021/0346150 A1    Nov. 11, 2021

Related U.S. Application Data

(63) Continuation of application No. 16/300,189, filed as application No. PCT/US2017/031948 on May 10, 2017, now Pat. No. 11,045,307.
(Continued)

(51) Int. Cl.
*A61F 2/12* (2006.01)
*B29C 33/42* (2006.01)
(Continued)

(52) U.S. Cl.
CPC .............. *A61F 2/12* (2013.01); *A61L 27/18* (2013.01); *A61L 27/50* (2013.01);
(Continued)

(58) Field of Classification Search
CPC .................. A61F 2/12; A61F 2/30942; A61F 2210/0014; A61F 2220/0008;
(Continued)

(56) References Cited

U.S. PATENT DOCUMENTS 3,761,047 A    9/1973 Mao
4,278,630 A *  7/1981 Scheicher .......... A61C 13/0003
                                                    264/225
(Continued)

FOREIGN PATENT DOCUMENTS

CA    3023507    11/2017
CN    102176883   9/2011
(Continued)

OTHER PUBLICATIONS

"Israel Application Serial No. 262831, Response filed Sep. 28, 2022 to Notification of Defects in Patent Application dated Apr. 24, 2022", w English Translation, 5 pgs.
(Continued)

*Primary Examiner* — Suzette J Gherbi
(74) *Attorney, Agent, or Firm* — SCHWEGMAN LUNDBERG & WOESSNER, P.A.

(57) ABSTRACT

Medical implants comprising biocompatible materials and having surface features that may assist in biocompatibility upon implantation in the body are described. Methods for manufacturing such implants are also described. The manufacturing process may include applying a biocompatible material to a texturized surface of a mold. The implants may include various features to assist their positioning, fixation, and/or identification during and/or after implantation.

20 Claims, 10 Drawing Sheets

Related U.S. Application Data

(60) Provisional application No. 62/410,121, filed on Oct. 19, 2016, provisional application No. 62/334,667, filed on May 11, 2016.

(51) Int. Cl.

| | |
|---|---|
| *A61L 27/18* | (2006.01) |
| *A61L 27/50* | (2006.01) |
| *B29C 33/38* | (2006.01) |
| *B29L 31/00* | (2006.01) |
| *A61F 2/30* | (2006.01) |

(52) U.S. Cl.
CPC ........ *B29C 33/3842* (2013.01); *B29C 33/424* (2013.01); *A61F 2/30942* (2013.01); *A61F 2210/0014* (2013.01); *A61F 2220/0008* (2013.01); *A61F 2240/001* (2013.01); *A61F 2250/0025* (2013.01); *A61F 2250/0085* (2013.01); *A61F 2250/0098* (2013.01); *B29L 2031/7532* (2013.01)

(58) Field of Classification Search
CPC ....... A61F 2240/001; A61F 2250/0025; A61L 27/50; B29C 33/3842; B29C 33/424
See application file for complete search history.

(56) References Cited

U.S. PATENT DOCUMENTS

| | | | |
|---|---|---|---|
| 4,533,568 | A | 8/1985 | McClinton et al. |
| 9,808,338 | B2 | 11/2017 | Schuessler et al. |
| 10,595,979 | B2 | 3/2020 | Bayat et al. |
| 10,912,636 | B2 | 2/2021 | Bayat et al. |
| 11,026,775 | B2 | 6/2021 | Bayat et al. |
| 11,045,307 | B2 | 6/2021 | Quirós et al. |
| 2002/0119177 | A1 | 8/2002 | Bowman et al. |
| 2004/0148024 | A1 | 6/2004 | Williams |
| 2004/0162613 | A1 | 8/2004 | Roballey |
| 2005/0216094 | A1* | 9/2005 | Prewett ............... B29C 41/14 428/34.1 |
| 2006/0219143 | A1 | 10/2006 | Brennan et al. |
| 2008/0171163 | A1* | 7/2008 | Caviezel ............ B29C 49/4242 425/522 |
| 2009/0088858 | A1 | 4/2009 | Zinger et al. |
| 2009/0125107 | A1 | 5/2009 | Maxwell |
| 2010/0081109 | A1 | 4/2010 | Schlottig et al. |
| 2010/0114303 | A1 | 5/2010 | Su et al. |
| 2010/0114310 | A1 | 5/2010 | Masaki |
| 2010/0016989 | A1 | 6/2010 | Lyngstadaas et al. |
| 2010/0226943 | A1 | 9/2010 | Brennan et al. |
| 2011/0009960 | A1* | 1/2011 | Altman ................. A61F 2/12 623/8 |
| 2011/0264213 | A1* | 10/2011 | DeMiranda ......... A61F 2/0059 623/8 |
| 2011/0276134 | A1 | 11/2011 | Manesis et al. |
| 2011/0276136 | A1 | 11/2011 | Koole et al. |
| 2012/0010636 | A1* | 1/2012 | Boey ................... A61L 31/10 606/151 |
| 2012/0046736 | A1* | 2/2012 | Su ...................... A61F 2/82 623/1.46 |
| 2012/0116502 | A1* | 5/2012 | Su ...................... A61F 2/0077 623/1.46 |
| 2012/0165934 | A1 | 6/2012 | Schuessler |
| 2012/0267334 | A1 | 10/2012 | Yamashita et al. |
| 2012/0277860 | A1 | 11/2012 | Dvir et al. |
| 2013/0110243 | A1 | 5/2013 | Patterson et al. |
| 2013/0190699 | A1 | 6/2013 | Stephan |
| 2013/0190870 | A1* | 7/2013 | Padsalgikar ............ A61L 27/18 427/2.24 |
| 2014/0074237 | A1* | 3/2014 | Yacoub ................. A61F 2/12 623/8 |
| 2015/0282926 | A1* | 10/2015 | Chacon Quiros ......... A61F 2/12 623/8 |
| 2017/0049549 | A1* | 2/2017 | Bayat .................. A61F 2/12 |
| 2018/0200045 | A1* | 7/2018 | Van Epps ............ A61F 2/12 |
| 2019/0142574 | A1 | 5/2019 | Quirós et al. |
| 2019/0290382 | A1* | 9/2019 | Martinez .............. A61B 90/02 |
| 2023/0233307 | A1* | 7/2023 | Contiliano ........... A61F 2/0077 623/8 |

FOREIGN PATENT DOCUMENTS

| | | |
|---|---|---|
| CN | 102176884 | 9/2011 |
| CN | 103037809 | 4/2013 |
| CN | 103997988 A | 8/2014 |
| CN | 108289753 | 7/2018 |
| CN | 108697416 | 10/2018 |
| CN | 109475404 | 3/2019 |
| CN | 109843210 | 6/2019 |
| CN | 109475404 | 8/2022 |
| EP | 0850604 A2 | 7/1998 |
| EP | 3454783 | 3/2019 |
| HK | 40001753 | 4/2023 |
| IL | 262831 | 12/2018 |
| JP | H0978102 A | 3/1997 |
| JP | H11240047 A | 9/1999 |
| KR | 10-2012-0107945 A | 10/2012 |
| KR | 20120107845 | 10/2012 |
| KR | 10-2012-0123093 A | 11/2012 |
| KR | 20190008252 | 1/2019 |
| WO | WO 2004/008983 A1 | 1/2004 |
| WO | WO 2009/046425 A2 | 4/2009 |
| WO | WO 2011/097499 A1 | 8/2011 |
| WO | WO 2011/127395 | 10/2011 |
| WO | WO 2013/070290 A1 | 11/2011 |
| WO | WO 2013/151755 | 10/2013 |
| WO | WO 95/03752 A1 | 2/2015 |
| WO | WO 2015/121686 A1 | 8/2015 |
| WO | WO 2017/093528 A1 | 6/2017 |
| WO | 2017196973 | 11/2017 |
| WO | 2017196973 | 1/2018 |

OTHER PUBLICATIONS

"Chinese Application Serial No. 202210933922.2, Voluntary Amendment filed Mar. 9, 2023", w English claims, 27 pgs.

"Korean Application Serial No. 10-2022-7028740, Response filed May 10, 2023 to Notice of Preliminary Rejection dated Nov. 18, 2022", w English claims, 35 pgs.

Barnsley, G.P. et al., "Textured surface breast implants in the prevention of capsular contracture among breast augmentation patients: a meta-analysis of randomized controlled trials," *Plast. Reconstr. Surg.*, vol. 117, No. 7, pp. 2182-2190 (2006), abstract only.

Barr. S. et al., "Current Implant Surface Technology: An Examination f Their Nanostructure and Their Influence on Fibroblast Alignment and Biocompatibility," *ePlasty*, vol. 9, pp. 198-217 (2009).

Barr, S. et al., "Patterning of Novel Breast Implant Surfaces by Enhancing Silicone Biocompatibility Using Biomimetic Topographies," *ePlasty*, vol. 10, pp. 246-268 (2010).

Barr, S. et al., "Breast implant surface development: perspectives on development and manufacture," *Aesthet. Surg. J.*, vol. 31, No. 1, pp. 56-67 (2011).

Barr, S. et al., "Development, Fabrication and Evaluation of a Novel Biomimetic Human Breast Tissue Derived Breast Implant Surface," *Acta Biomaterialia*, vol. 49, pp. 260-271 (2017).

Barr, S. et al., "Functional Biocompatibility Testing of Silicone Breast Implants and a Novel Classification System Based on Surface Roughness," *J. Mech. Behavior Biomed. Mater.*, vol. 75, pp. 75-81 (2017).

Castel, N. et al., "Polyurethane-coated breast implants revisited: a 30-year follow-up," *Arch. Plast. Surg.*, vol. 42, No. 2, pp. 186-193 (2015).

D'Andrea, F. et al., "Modification of cysteinyl leukotriene receptor expression in capsular contracture: Preliminary results," *Ann. Plast. Surg.*, vol. 58, No. 2, pp. 212-213 (2007), abstract only.

Davila, A. et al., "Human Acellular Dermis Versus Submuscular Tissue Expander Breast Reconstruction: A Multivariate Analysis of Short-Term Complications," *Archives of Plastic Surgery*, vol. 40, pp. 19-27 (2013).

(56) References Cited

OTHER PUBLICATIONS

Del Campo et al., "Fabrication approaches for generating Complex Micro—and Nanopatterns on Polymeric Surfaces," *Chem. Rev.*, vol. 108, pp. 911-945 (2008).

Derby, B.M. et al., "Textured silicone breast implant use in primary augmentation: core data update and review," *Plast. Reconstr. Surg.*, vol. 135, No. 1, pp. 113-124 (2015).

Efanov, J.I. et al., "Breast-implant texturing associated with delamination of capsular layers: A histological analysis of the double capsule phenomenon," *Ann. Chir. Plast. Esthet.*, vol. 62, No. 3, pp. 196-201 (2017).

Ferret et al., "Clarification of Cereplas Breast Implant Manufacturing Processes," *Aesthetic Surgery Journal*, vol. 31, p. 725 (2011).

Flemming, R.G. et al., "Effects of synthetic micro—and nano-structured surfaces on cell behavior," Biomaterials, vol. 20, No. 6, pp. 573-588 (1999).

Gabriel, A. et al., "The Evolution of Breast Implants," *Clin. Plast. Surg.*, vol. 42, No. 4, pp. 399-404 (2015).

Garabádian, C. et al., "A Multi-Topographical-Instrument Analysis: The Breast Implant Texture Measurement," *Surf. Topogr.: Metrol. Prop.*, vol. 5, pp. 1-12 (2017).

Glicksman, C.A. et al., "A Step Forward Toward the Understanding of the Long-Term Pathogenesis of Double Capsule Formation in Macrotextured Implants: A Prospective Histological Analysis," *Aesthet. Surg. J.*, vol. 39, No. 11, pp. 1191-1199 (2018).

Harvey et al., "Designing Implant Surface Topography for Improved Biocompatibility," *Expert Rev. Med. Devices*, vol. 10, pp. 1-11 (2013).

Headon, H. et al., Capsular Contracture after Breast Augmentation: An Update for Clinical Practice, *Arch. Plast. Surg.*, vol. 42, No. 5, pp. 532-543 (2015).

"Implant Surfaces Analyzed," The University of Manchester, 2012 (approximate).

Kyle, D.J. et al., "Identification of molecular phenotypic descriptors of breast capsular contracture formation using informatics analysis of the whole genome transcriptome," *Wound Repair Regen.*, vol. 21, No. 5, pp. 762-769 (2013), abstract only.

Kyle, D. et al., "Development and Functional Evaluation of Biomimetic Silicone Surfaces with Hierarchical Micro/Nano-topographical Features Demonstrates Favourable in vitro Foreign Body Response of Breast-Derived Fibroblasts," *Biomaterials*, vol. 52, pp. 88-102 (2015).

Laboratoire national de métrologie et d'essais (LNE) Test Report, File L050836—Document DE/2, Dec. 8, 2010 (33 pages).

Laboratoire national de métrologie et d'essais (LNE) Test Report, File L050836—Document DE/3, Dec. 8, 2010 (33 pages).

Laboratoire national de métrologie et d'essais (LNE) Test Report, File L050836—Document DE/4, Dec. 8, 2010 (33 pages).

Liu, D.Z. et al., "Comparison of Outcomes Using AlloDerm Versus FlexHD for Implant-Based Breast Reconstruction," *Annals of Plastic Surgery* (2013).

Maxwell, G.P. et al., "Benefits and Limitations of Macrotextured Breast Implants and Consensus Recommendations for Optimizing Their Effectiveness," *Aesthet. Surg. J.*, vol. 34, No. 6, pp. 876-881 (2014).

Mempin, M. et al., "The A, B and C's of Silicone Breast Implants: Anaplastic Large Cell Lymphoma, Biofilm and Capsular Contracture," *Materials*, vol. 11, pp. 1-11. doi:10.3390/ma11122393 (2018).

Mendonca, G. et al., "Advancing dental implant surface technology—from micron—to nanotopography," *Biomaterials*, vol. 29, No. 28, pp. 3822-3835 (2008), abstract only.

Militky, J. et al., "Surface Roughness and Fractal Dimension," *The Journal of the Textile Institute*, vol. 92, pp. 91-113 (2001).

Munhoz, A.M. et al., "Nanotechnology, nanosurfaces, and silicone gel breast implants: current aspects," *Case Reports Plast. Surg. Hand Surg.*, vol. 4, No. 1, pp. 99-113 (2017).

Rompen, E. et al., "The effect of material characteristics, of surface topography and of implant components and connections on soft tissue integration: a literature review," *Clin. Oral Implants Res.*, vol. 17, Suppl. 2, pp. 55-67 (2006).

Salzberg, C.A. et al., "Immediate Breast Reconstruction using Porcine Acellular Dermal Matrix (Strattice): Long-term Outcomes and Complications," *Journal of Plastic, Reconstructive & Aesthetic Surgery*, vol. 66, pp. 323-328 (2013).

Schulte, V.A. et al., "Surface topography induces fibroblast adhesion on intrinsically nonadhesive poly(ethylene glycol) substrates," *Biomacromolecules*, vol. 10, No. 10, pp. 2795-2801 (2009), abstract only.

Seth, A.K. et al., "A Comparative Analysis of Cryopreserved versus Prehydrated Human Acellular Dermal Matrices in Tissue Expander Breast Reconstruction," *Annals of Plastic Surgery*, vol. 70, pp. 632-635 (2013).

Sforza, M. et al., "A Preliminary Assessment of the Predictability of Fat Grafting to Correct Silicone Breast Implant-Related Complications," *Aesthetic Surgery Journal*, vol. 36, pp. 886-894 (2016).

Sforza, M. et al., "The $21^{st}$ Century Silicone Breast Implant," *J. Surg. Open Access*, vol. 2, pp. 1-2 (2016).

Sforza, M. et al., "Preliminary 3-Year Evaluation of Experience With SilkSurface and VelvetSurface Motiva Silicone Breast Implants: A Single-Center Experience With 5813 Consecutive Breast Augmentation Cases," *Aesthetic Surgery Journal*, vol. 38, pp. 562-573 (2018).

Shih, B. et al. "Identification of novel keloid biomarkers through profiling of tissue biopsies versus cell cultures in keloid margin specimens compared to adjacent normal skin," *Eplasty*, vol. 10, pp. 187-202 (2010).

Shih, B. et al., "Comparative genomic hybridisation analysis of keloid tissue in Caucasians suggests possible involvement of HLA-DRB5 in disease pathogenesis," *Arch. Dermatol. Res.*, vol. 304, No. 3, pp. 241-249 (2012), abstract only.

Stevens, W.G. et al., "Risk factor analysis for capsular contracture: a 5-year Sientra study analysis using round, smooth, and textured implants for breast augmentation," *Plast. Reconstr. Surg.*, vol. 132, No. 5, pp. 1115-1123 (2013).

Syed, F. et al., "Fibroblasts from the growing margin of keloid scars produce higher levels of collagen I and III compared with intralesional and extralesional sites: clinical implications for lesional site-directed therapy," *Br. J. Dermatol.*, vol. 164, No. 1, pp. 83-96 (2011), abstract only.

Tan, K.T. et al., "Tumour necrosis factor-α expression is associated with increased severity of periprosthetic breast capsular contracture," *Eur. Surg. Res.*, vol. 45, Nos. 3-4, pp. 327-332 (2010), abstract only.

Tan et al., "Hyaluronan, TSG-6, and Inter-α-Inhibitor in Periprosthetic Breast Capsules: Reduced Levels of Free Hyaluronan and TSG-6 Expression in Contracted Capsules," *Aesthetic Surgery Journal*, vol. 31, pp. 47-55 (2011).

Valencia-Lazcano, A. et al., "Characterization of Breast Implant Surfaces and Correlation with Fibroblast Adhesion," *Journal of the Mechanical Behavior of Biomedical Materials*, vol. 21, pp. 133-148 (2013).

International Search Report in PCT/US2017/031948 dated Dec. 4, 2017 (3 pages).

"Brazilian Application Serial No. 112018072963-9, Office Action dated Jan. 6, 2022", w o English Translation, 4 pgs.

"Israel Application Serial No. 262831, Notification of Defects in Patent Application dated Apr. 24, 2022", w English translation, 4 pgs.

"Israel Application Serial No. 262831, Response filed Mar. 21, 2022 to Notification of Defects in Patent Application dated Oct. 11, 2021", w English Translation, 4 pgs.

"Israel Application Serial No. 262831, Office Action dated Oct. 11, 2021", W English Translation, 4 pgs.

"International Application Serial No. PCT US2017 031948, Invitation to Pay Additional Fees mailed Oct. 2, 2017", 8 pgs.

"International Application Serial No. PCT US2017 031948, Written Opinion dated Dec. 4, 2017", 8 pgs.

"International Application Serial No. PCT US2017 031948, International Preliminary Report on Patentability dated Nov. 22, 2018", 10 pgs.

"Application Serial No. 16 300,189, Preliminary Amendment filed Nov. 9, 2018", 3 pgs.

"Application Serial No. 16 300,189, Non Final Office Action dated May 11, 2020", 9 pgs.

(56) References Cited

OTHER PUBLICATIONS

"Application Serial No. 16 300,189, Response filed Sep. 11, 2020 to Non Final Office Action dated May 11, 2020", 9 pgs.

"Application Serial No. 16 300,189, Examiner Interview Summary dated Sep. 1, 2020", 3 pgs.

"Application Serial No. 16 300,189, Notice of Allowance dated Nov. 10, 2020", 5 pgs.

"Application Serial No. 16 300,189, Notice of Allowance dated Feb. 23, 2021", 5 pgs.

"Application Serial No. 16 300,189, Corrected Notice of Allowability dated Mar. 31, 2021", 2 pgs.

"Application Serial No. 16 300,189, Supplemental Notice of Allowability dated Apr. 30, 2021", 2 pgs.

"Brazilian Application Serial No. 112018072963-9, Response filed Apr. 14, 2022 to Office Action dated Jan. 6, 2022", 36 pgs.

"European Application Serial No. 17725413.3, Response to Communication pursuant to Rules 161(1) and 162 EPC filed Jun. 28, 2019", 44 pgs.

"European Application Serial No. 17725413.3, Communication Pursuant to Article 94(3) EPC dated Sep. 28, 2021", 4 pgs.

"European Application Serial No. 17725413.3, Response filed Feb. 8, 2022 to Communication Pursuant to Article 94(3) EPC dated Sep. 28, 2021", 11 pgs.

"Korean Application Serial No. 10-2018-7033752, Notice of Final Rejection dated Jan. 11, 22", w English Translation, 7 bgs.

"Chinese Application Serial No. 201780028991.6, Office Action dated Apr. 23, 2020", w English translation, 9 pgs.

"Chinese Application Serial No. 201780028991.6, Response filed Sep. 8, 2020 to Office Action dated Apr. 23, 2020", w o English claims, 4 pgs.

"Chinese Application Serial No. 201780028991.6, Office Action dated Jan. 28, 2021", w English translation, 13 pgs.

"Canadian Application Serial No. 3023507, Examiners Rule 86(2) Requisition dated Jul. 26, 2023", 6 pgs.

\* cited by examiner

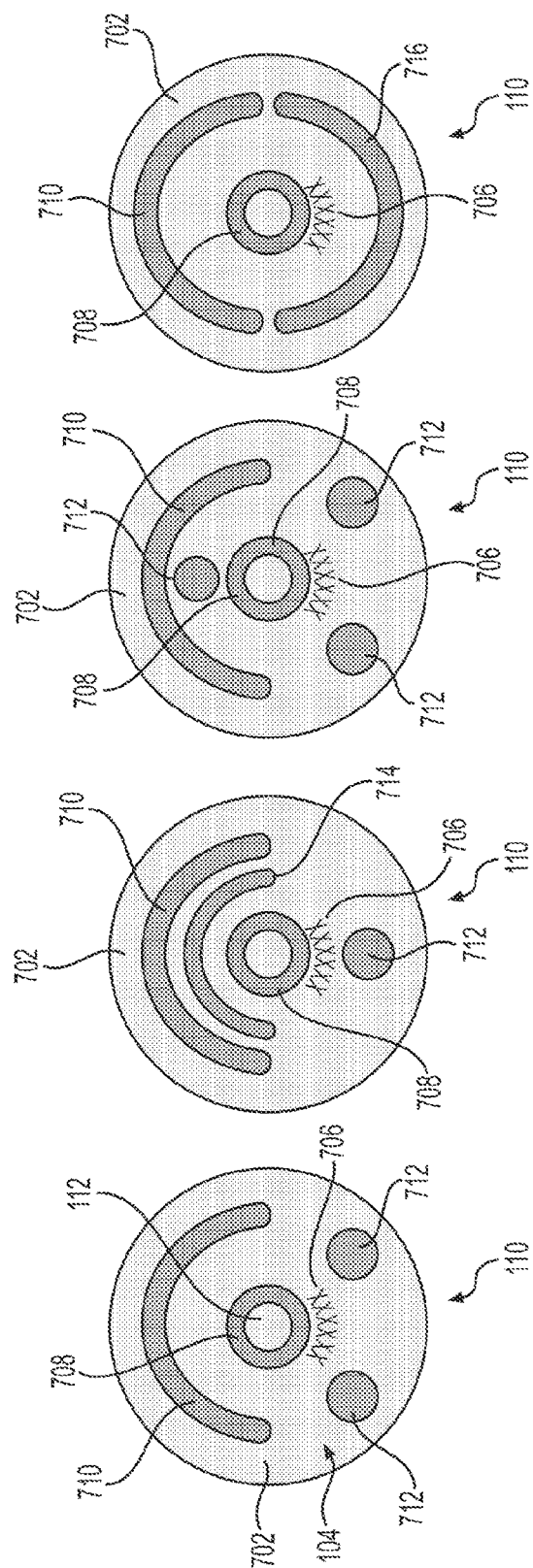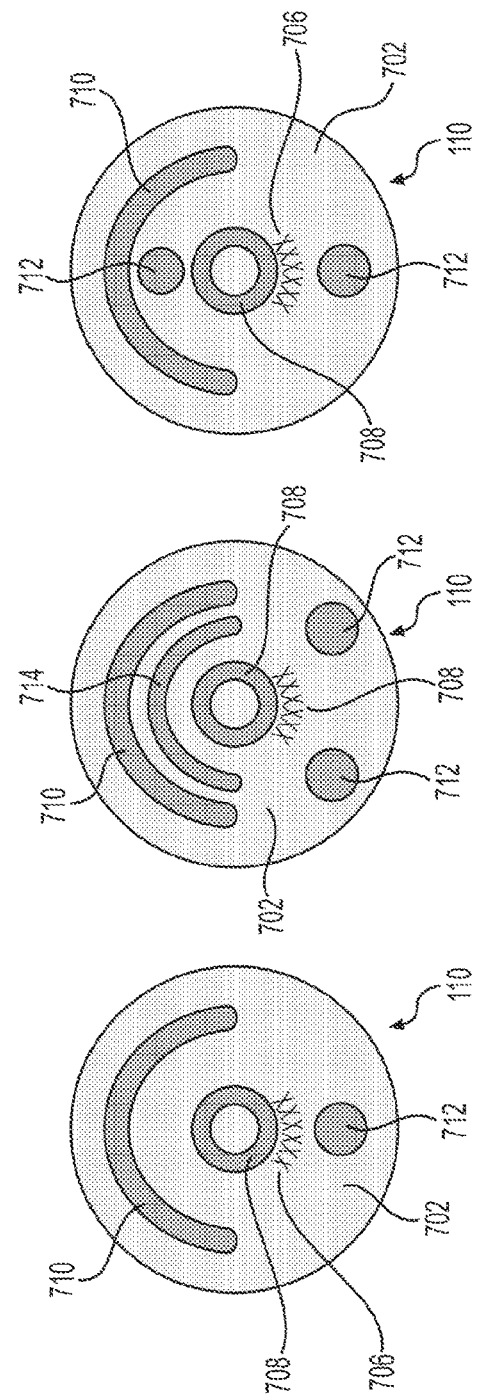

| VARIABLES | | | | | |
|---|---|---|---|---|---|
| SHAPE | HEIGHT | WIDTH | PROJECTION | APEX POSITION | UPPER POLE |
| 1102 | 1106 | 1108 | 1110 | 1112 | 1114 |
| 1104 | 1106 | 1108 | 1110 | 1112 | 1116 |

*FIG. 11*

MEDICAL IMPLANTS AND METHODS OF PREPARATION THEREOF

CROSS-REFERENCE TO RELATED APPLICATIONS

This application is a continuation of U.S. application Ser. No. 16/300,189, filed on Nov. 9, 2018, as the U.S. national stage entry of International Application No. PCT/US2017/031948, filed on May 10, 2017, which claims priority to U.S. Provisional Application No. 62/334,667, filed on May 11, 2016; and U.S. Provisional Application No. 62/410,121, filed on Oct. 19, 2016, each of which is incorporated by reference herein in its entirety.

TECHNICAL FIELD

The present disclosure generally relates to medical implants, their surface characteristics, and methods of their manufacture and customization.

BACKGROUND

Many people have medical implants for medical and/or esthetic purposes. For example, mammary implantation is a common medical/esthetical procedure in many parts of the world. Often, women who have suffered from breast cancer or mammary hypoplasia (for example due to a lack of, or damage to, mammary tissue) opt for mammary implantation. However, breast implants and other medical implants can present significant and disruptive physiological effects in the surrounding tissues, including effects detectable from outside of the body. Due to the relatively high volume, mass, and surface area of breast implants, the location of breast implants proximate to the chest cavity, and the potential for incompatibility with living human tissue, satisfactory long-term implantation of breast implants can present challenges.

The body's natural response to foreign objects is either to destroy them or, when this is not possible, to encapsulate them in a process known as tissue encapsulation. Tissue encapsulation may occur after implantation of many implantable medical devices, including breast implants. When an implant is inserted into the body, the body may react to the foreign object by forming a fibrous membrane, or capsule, around it over time. In some cases, capsules that form around implants can shrink and cause a patient's tissue to feel harder, and may cause disfiguration and discomfort, e.g., due to the tightening of tissue from the tissue capsules. This is known as capsular contraction. With regard to breast implants, capsular contraction can cause disfiguration, hardness, and discomfort in the breast area. Moreover, breast and other implants can yield stresses and act as stimuli for other extra-cellular, immunological, and gene expression responses.

One cause of tissue encapsulation and other physiological responses to implant installation in a patient's body is a lack of, or relatively low degree of, implant surface biocompatibility. Many breast implants known in the art, for example, were designed to have a coarse surface in order to attach firmly to a patient's muscle tissue and stay in place. However, excessive friction between a coarse-surfaced implant and the surrounding tissue may cause the aforementioned tissue encapsulation and capsular contraction due to friction-induced tissue irritation. Uncontrolled implant surfaces may also be susceptible to bacterial colonization, e.g., in the form of biofilms that may develop over and within crevices in a coarse surface and/or due to debris on the implant surface remaining from the manufacturing process.

A further concern with regard to implant manufacturing is consistency. Implants often vary in terms of biocompatibility from manufacturer to manufacturer, implant model to model, and often from individual implant to implant. Such variation can lead to unpredictability in clinical outcomes of implantation surgeries, costly and painful diagnostic procedures, and subsequent surgeries in order to fix problematic implants. For example, one known method of manufacturing implant surfaces includes bombarding the surface with particles of salt or other solids, and then washing away the particles. Implants produced by this method, however, may exhibit variations in surface texture from one implant to the next, due to variations in individual salt or other particles and in the bombardment process. Further, the implant may also include remnants of particles that do not fully wash away, causing additional adverse effects on surrounding tissues. Such manufacturing processes provide little to no control over surface properties, not to mention a lack of reproducibility.

Implants, such as breast implants, also may migrate over time without proper positioning and fixation. Sutures, Dacron mesh, shell perforations, and various textures such as foams, rings, or ridges on the posterior side of the breast implant can result in adverse immunological responses, promoting in-growth of tissue and creating capsule contracture. Moreover, improper implantation and placement may result in deformation, stress, and fracture of the implant. Further, once inserted, implants may move out of position during and/or after surgery. Surgeons may not have a clear visual line to a site of implantation both during and after surgery, which may complicate accurate placement during surgery and monitoring of implants during recovery.

SUMMARY

The present disclosure includes implants with surface characteristics and/or fixation features that may provide for increased biocompatibility, safety, and/or longevity, as well as methods of making and customizing such implants, and compositions and materials suitable for such devices. While portions of this disclosure refer to breast implants, the methods and materials disclosed herein may be used to prepare other implantable medical devices, such as, e.g., other implants used in cosmetic and/or reconstruction procedures (e.g., gastric implants, gluteal implants, calf implants, testicular implants, penile implants), tissue expanders, pacemaker components (e.g., pacemaker covers) and other electro-stimulator implants, drug delivery ports, catheters, orthopedic implants, vascular and non-vascular stents, and other devices. Further, the methods herein may be used on molds (e.g., mandrels and other molds), extrusion tools, and other devices used to fabricate medical devices or components thereof.

The present disclosure includes, for example, a medical implant comprising a biocompatible material that defines a surface having a kurtosis value ranging from about 3.0 to about 7.0 or from about 3.0 to about 5.0, and an average roughness ranging from about 2.0 $\mu$m to about 6.0 $\mu$m, wherein the surface is an outermost surface of the implant. In some examples, the surface may have a skewness value ranging from about −0.2 to about 2.0, a plurality of peaks having an average height ranging from about 15 $\mu$m to about 35 $\mu$m, and/or a plurality of peaks distributed at a density ranging from about 20,000 peaks/cm$^2$ to about 65,000 peaks/cm$^2$. The biocompatible material of the implant may comprise a polymer or copolymer, such as an elastomer. For example, the biocompatible material may comprise silicone. According to some aspects, the implant may comprise a shell that defines a cavity, wherein the surface is an outer surface of the shell. The implant may comprise a biocompatible filling in at least a part of the cavity or filling the entire cavity.

Another exemplary implant of the present disclosure comprises a biocompatible material that defines a surface having an average roughness ranging from about 2.0 µm to about 6.0 µm, a skewness value ranging from about −0.2 to about 2.0, and a contact angle between about 90° and about 150°. The surface may also have a kurtosis value ranging from about 3.0 to about 5.0, a plurality of valleys having an average depth ranging from about 10 µm to about 26 µm, and/or a plurality of peaks distributed at a density ranging from about 30,000 peaks/cm$^2$ to about 60,000 peaks/cm$^2$. The surface of the implant may be an outermost surface of the implant, e.g., on the posterior side and/or the anterior side of the implant. The biocompatible material may comprise silicone and/or another polymer or copolymer. The surface of the implant form the outer portion of a shell of the implant, wherein the shell defines a cavity. According to some aspects of the present disclosure, the cavity may be at least partially or entirely filled with a biocompatible liquid or gel filling, such as, e.g., a saline liquid or a silicone gel.

The present disclosure also includes a medical implant comprising a silicone material that defines an outer surface of the implant, the surface having a kurtosis value ranging from about 3.0 to about 5.0, an average roughness ranging from about 2.0 µm to about 6.0 µm, and a positive skewness value (a skewness value greater than 0), wherein the surface includes a plurality of peaks distributed at a density ranging from about 20,000 peaks/cm$^2$ to about 65,000 peaks/cm$^2$, such as from about 40,000 peaks cm$^2$ to about 50,000 peaks/cm$^2$. The plurality of peaks may have an average height ranging from about 5 µm to about 50 µm, such as from about 10 µm to about 26 µm, or from about 15 µm to about 35 µm, for example. Additionally or alternatively the surface may comprise a plurality of valleys having an average depth ranging from about 5 µm to about 50 µm, such as from about 10 µm to about 26 µm, or from about 15 µm to about 35 µm. In some examples, the implant may have a kurtosis value ranging from about 3.0 to about 5.0, such as from about 3.5 to about 5.0, or from about 4.0 to about 5.0. The implant may optionally be a breast implant, a gastric implant, a gluteal implant, a calf implant, a testicular implant, a penile implant, or an electro-stimulator implant. The surface may be located on an anterior side or a posterior side of the implant. For example, the surface may be on the anterior side, and the posterior side of the implant may include a surface having an average roughness that is different from the average roughness of the surface on the anterior side of the implant.

The present disclosure also includes a medical implant comprising a silicone material that defines an outer surface of the implant, the outer surface having a kurtosis value ranging from about 3.0 to about 5.0, an average roughness ranging from about 2.0 µm to about 6.0 µm, and a skewness value ranging from 0 to about 1.0, and a plurality of peaks distributed at a density ranging from about 30,000 peaks/cm$^2$ to about 60,000 peaks/cm$^2$. The implant may be semi-rigid or flexible. In at least one example, the implant may include a shell, wherein the outer surface of the shell is the outer surface of the implant. The shell may define a cavity, for example, with a biocompatible filling in at least a part of the cavity.

In some aspects of the present disclosure, the implant may be a breast implant. For example, the breast implant may include a shell comprising a biocompatible material such as silicone or other biocompatible material, wherein the biocompatible material defines a surface having a kurtosis value ranging from about 3.0 to about 7.0, and wherein the shell defines a cavity. In some examples, the cavity may include a liquid or gel filling material such as, e.g., a saline liquid or a silicone gel. The surface may also have an average roughness ranging from about 2.0 µm to about 6.0 µm and/or a skewness value ranging from about −0.2 to about 2.0. In at least one example, the surface may include a plurality of peaks distributed at a density ranging from about 20,000 peaks/cm$^2$ to about 65,000 peaks/cm$^2$ and/or having an average height ranging from about 15 µm to about 35 µm. The surface of the breast implant may include an anterior side and a posterior side, the posterior side being closer to a chest cavity of a patient upon implantation. In at least one example, an entirety of the anterior side may have a kurtosis value ranging from about 3.0 to about 5.0, or from about 4.0 to about 5.0. The surface may be an outer surface of a shell of the implant, and the shell may include an inner surface having an average roughness higher than an average roughness of the outer surface. In some examples, the implant may include a patch.

Another exemplary breast implant of the present disclosure comprises a biocompatible material defining a shell comprising an inner surface and an outer surface, wherein the outer surface has a kurtosis value ranging from about 3.0 to about 7.0 and an average roughness ranging from about 2.0 µm to about 6.0 µm, and the inner surface has an average roughness that is higher than the average roughness of the outer surface. The outer surface may have a positive skewness value, such as a skewness value ranging from 0 to about 1.0, from 0 to about 0.2, or from about 0.2 to about 1.0. According to some aspects of the present disclosure, the outer surface may include a plurality of peaks distributed at a density ranging from about 30,000 peaks/cm$^2$ to about 60,000 peaks/cm$^2$, such as from about 40,000 peaks/cm$^2$ to about 50,000 peaks/cm$^2$. The breast implant also may include a filling inside the shell, such as a liquid filling or a gel filling. In some examples, the breast implant may comprise a radiopaque material. For example, at least one of the shell or the filling may include a radiopaque material, e.g., the filling may comprise a liquid or gel that comprises a radiopaque salt and/or the shell may include at least one radiopaque marker. In some aspects, the filling may be a gel with a penetration value ranging from about 5.0 to about 6.0. Additionally or alternatively, the biocompatible material defining the shell may comprise silicone, and/or the shell may have an elongation value ranging from about 650% to about 750%.

The present disclosure also includes a breast implant that includes a shell comprising a silicone material, wherein the shell defines an outer surface of the implant, the outer surface having an average roughness ranging from about 3.0 µm to about 4.0 µm, and wherein the outer surface includes a plurality of peaks distributed at a density ranging from about 40,000 peaks/cm$^2$ to about 50,000 peaks/cm$^2$. The breast implant may also include a filling inside the shell, such as a liquid or a gel. In at least one example, the shell and/or the filling may include a radiopaque material. the shell may include a patch affixed to the shell such that an outer surface of the patch is flush with the outer surface of the shell. According to some aspects of the present disclosure, the inner surface of the shell may have an average roughness greater than the average roughness of the outer surface of the shell. At least one of the shell or the filling may include a radiopaque material, such as a radiopaque salt and/or one or more radiopaque markers. In at least one example, the shell may include a patch affixed to the shell such that an outer surface of the patch is flush with the outer surface of the shell. The patch may comprise silicone or another biocompatible material.

The present disclosure also includes a breast implant comprising a shell that comprises a silicone material, wherein the shell includes an inner surface and an outer surface, the outer surface having a kurtosis value ranging from about 3.0 to about 5.0, an average roughness ranging from about 2.5 µm to about 4.5 µm, a skewness value ranging from about 0.2 to about 1.0, and a plurality of peaks distributed at a density ranging from about 30,000 peaks/$cm^2$ to about 60,000 peaks/$cm^2$. The breast implant also includes a filling comprising a silicone material inside the shell, and a radiopaque material. The shell may have an elongation value ranging from about 650% to about 750%, and/or the filling may comprise a silicone gel having a penetration value ranging from about 5.0 to about 6.0. In at least one example, the inner surface may have an average roughness that is higher than the outer surface. The outer surface may include an anterior side and a posterior side, the posterior side being closer to a chest cavity of a patient upon implantation. According to some aspects of the present disclosure, the posterior side of the breast implant may include a label, e.g., with information useful for identifying various features of the breast implant.

The present disclosure also includes methods of manufacturing implants, such as breast implants and other medical implants, including those described above and elsewhere herein. In at least one example, the method includes applying a biocompatible material to a surface of a mold to form a shell of the implant, wherein the surface of the mold has a texture that provides a first surface of the shell with an average roughness value ranging from about 2.0 µm to about 6.0 µm and a skewness value ranging from about −0.2 to about 2.0. The first surface of the shell may also have a kurtosis value ranging from about 3.0 to about 7.0, and/or a plurality of peaks distributed at a density ranging from about 20,000 peaks/$cm^2$ to about 65,000 peaks/$cm^2$. The biocompatible material may comprise one or more polymers and/or copolymers. For example, the biocompatible material may comprise a silicone polymer.

According to some aspects of the present disclosure, the texture of the mold may be produced by contacting the surface of the mold with a plurality of particles, e.g., abrasive particles. In some examples, the particles may have an average diameter ranging from about 50 µm to about 250 µm, such as from about 100 µm to about 200 µm. Additionally or alternatively, the particles may have a Mohs hardness ranging from about 5.0 to about 8.0, or from about 6.0 to about 7.0. According to some aspects of the present disclosure, the plurality of particles may include particles with a rounded shape and/or particles with a subangular shape. The shell of the implant may have a thickness ranging from 0.1 mm to about 1.2 mm, such as from about 0.2 mm to about 0.5 mm, or from about 0.5 mm to about 1.0 mm.

The method may also include one or more steps of: texturizing a second surface of the shell opposite the first surface, such that the second surface has a higher average roughness than the first surface; curing the shell; removing the shell from the mold; inverting the shell to form a cavity, such that the first surface of the shell defines an outermost surface of the shell; introducing a biocompatible filling into the cavity to contact the second surface of the shell; and/or covering an aperture of the shell with a patch. In at least one example, applying the biocompatible material to the surface of the mold may include applying a first silicone dispersion to the mold, followed by applying a second silicone dispersion over the first silicone dispersions. The second silicone dispersion may be the same or different from the first silicone dispersion. At least one of the first and second silicone dispersions may contain a pigment to form a colored layer of the shell, the colored layer being a low diffusion barrier layer, e.g., to prevent or inhibit a material from passing through the shell.

In some examples disclosed herein, the method of manufacturing the implant includes applying a biocompatible material to a texturized surface of a mold to form a shell of the implant; and removing the shell from the mold, wherein a surface of the shell formerly in contact with the texturized surface of the mold has a kurtosis value ranging from about 3.0 to about 7.0. The surface of the shell formerly in contact with the texturized surface of the mold may also have one or more of: a skewness value ranging from about −0.2 to about 2.0; an average roughness value ranging from about 2.0 µm to about 6.0 µm; and/or a plurality of peaks distributed at a density ranging from about 20,000 peaks/$cm^2$ to about 65,000 peaks/$cm^2$. According to some aspects of the present disclosure, the mold may comprise a polymer or a copolymer and/or the biocompatible material may comprise silicone. The implant may be a breast implant, for example. The method may also include one or more steps of: applying multiple layers of the biocompatible material to the surface of the mold; texturizing an exposed surface of the biocompatible material before removing the shell from the mold such that the texturized exposed surface has a higher average roughness than the surface of the shell formerly in contact with the mold; curing the biocompatible material; inverting the shell to form a cavity, such that the surface of the shell formerly in contact with the texturized surface of the mold defines an outermost surface of the shell; introducing a biocompatible filling into the cavity through an aperture of the shell to contact an innermost surface of the shell; and/or covering the aperture of the shell with a patch.

The present disclosure also includes a method of manufacturing a medical implant by applying a biocompatible material to a texturized surface of a mold to form a shell of the implant, curing the shell, and removing the shell from the mold, wherein a surface of the shell formerly in contact with the texturized surface of the mold has an average roughness value ranging from about 2.0 µm to about 6.0 µm. The surface of the shell formerly in contact with the texturized surface of the mold may also have a kurtosis value ranging from about 3.0 to about 7.0; a skewness value ranging from about −0.2 to about 2.0; and/or a plurality of peaks distributed at a density ranging from about 20,000 peaks/$cm^2$ to about 65,000 peaks/$cm^2$, such as from about 30,000 peaks/$cm^2$ to about 50,000 peaks/$cm^2$, or from about 40,000 peaks/$cm^2$ to about 50,000 peaks/$cm^2$. The method may include introducing a biocompatible filling into the cavity to contact an innermost surface of the shell.

According to a further example, the present disclosure includes a method of manufacturing a medical implant comprising dipping a texturized surface of a mold into a silicone dispersion at least two times to form a shell of the implant; curing the shell; removing the shell from the mold; inverting the shell to form a cavity having an aperture, such that a surface of the shell formerly in contact with the texturized surface of the mold defines an outermost surface of the shell having an average roughness ranging from about 2.0 µm to about 6.0 µm, a skewness value ranging from about −0.2 to about 2.0, and a plurality of peaks distributed at a density ranging from about 20,000 peaks/cm$^2$ to about 65,000 peaks/cm$^2$; introducing a biocompatible liquid or biocompatible gel into the cavity; and affixing a patch over the aperture, wherein the implant is a breast implant.

The present disclosure also includes implants that include features to assist in maintaining a position of the implant once implanted inside a patient. For example, the present disclosure includes breast implants having features, including various surface features, configured to restrict the movement of the implants relative to adjacent tissues. The breast implants may include any of the features of breast implants or other implants discussed above and disclosed elsewhere herein.

In at least one such example, the breast implant includes a shell having a posterior side configured to face a chest cavity of a patient upon implantation and an anterior side opposite the posterior side, wherein the posterior side includes at least one surface feature configured to restrict movement of the breast implant relative to surrounding tissue post-implantation, the at least one surface feature including: a first surface having a first surface texture and at least one second surface having a second surface texture different than the first surface texture; a support element extending outward from the shell; or a combination thereof. The posterior side of the shell may include the first surface and the at least one second surface, wherein the first surface has a first average roughness and the at least one second surface has a second average roughness that is greater than the first average roughness. According to some aspects of the present disclosure, the first average roughness may range from about 2.0 µm to about 6.0 µm. Additionally or alternatively, the at least one second surface may include at least two second surfaces surrounded by the first surface, wherein the at least two second surfaces may be the same or different sizes. In at least one example, the first surface may have a kurtosis value ranging from about 3.0 to about 5.0, such as from about 3.5 to about 5.0, or from about 4.0 to about 5.0. In some aspects, the support element may have a first end extending from the shell and a second end configured for attachment to an anatomical feature of the patient. The support element may include, for example, a flexible strap. In some examples, the shell may have an elongation value ranging from about 650% to about 750%.

According to some aspects of the present disclosure, the posterior side of the shell may include the first surface and the at least one second surface, the first surface having an average roughness ranging from about 2.0 µm to about 6.0 µm, and the at least one second surface having an average roughness greater than the average roughness of the first surface. The first surface and the at least one second surface may be integral portions of an outer surface of the shell and/or have the same chemical composition. Additionally or alternatively, one or more of the second surfaces may be defined by a tab coupled to the shell. For example, the posterior side of the shell may include at least one tab, e.g., a plurality of tabs, coupled to the shell, wherein an outer surface of each tab defines a second surface of the at least one second surface of the posterior side. Exemplary materials suitable for the tabs(s) include, but are not limited to, silicone.

The present disclosure also includes a breast implant comprising a shell having a posterior side configured to face a chest cavity of a patient upon implantation and an anterior side opposite the posterior side, wherein the posterior side includes: a first surface having an average roughness ranging from about 2.0 µm to about 15.0 µm, such as from about 2.0 µm to about 6.0 µm; and at least one second surface having an average roughness greater than the average roughness of the first surface; wherein the first surface and the at least one second surface of the posterior side form a pattern for restricting movement of the breast implant relative to surrounding tissue post-implantation in the patient. In some examples, a surface of the anterior side of the shell may have a same average roughness as the first surface and/or the at least one second surface of the posterior side of the shell. The at least one second surface may include one or more surfaces having a circular shape, an oval shape, an arched shape, and/or a shape of a ring. In at least one example, the shell may include at least one second surface having an arched shape located on an upper portion of the posterior side of the shell, e.g., for contacting an upper portion of the chest cavity of the patient upon implantation. The at least one second surface may be an integral portion of the shell, and/or may be defined by an outer surface of a tab coupled to the shell. In at least one example, the at least one second surface may include at least three second surfaces each surrounded by the first surface. In some aspects, the posterior side of the shell may include a third surface having an average roughness different from the average roughness of the first surface and the at least one second surface. The third surface may include one or more surface features of the implants discussed above and elsewhere herein. Further, for example, a surface of the anterior side of the shell may have an average roughness the same as the average roughness of the first surface, the at least one second surface, and/or the at least one third surface. In some examples, the at least one second surface may include a plurality of second surfaces including at least one second surface located on an upper portion of the posterior side of the shell and having an arched shape with a center of curvature at or proximate a center of the posterior side, and at least one second surface in a shape of a ring centered on the posterior side. Additionally or alternatively, the anterior and/or posterior side of the shell may include one or more labels.

The present disclosure also includes a breast implant comprising a shell having a posterior side configured to face a chest cavity of a patient upon implantation and an anterior side opposite the posterior side, wherein the posterior side includes: a first surface having a first surface texture; and a plurality of second surfaces each having a second surface texture different than the first surface texture, the plurality of second surfaces including a second surface spanning an upper portion of the posterior side and having an arched shape with a center of curvature at or proximate a center of the posterior side; wherein the shell is made at least partly from silicone and has an elongation value ranging from about 650% to about 750%. In some examples, the at least one second surface may include a plurality of second surfaces, each second surface being an integral portion of the shell or being defined by an outer surface of a tab coupled to the shell. Additionally or alternatively, the posterior side of the shell may include a label. The breast implant may include one or more other features of the breast implants and/or other implants discussed above or elsewhere herein.

The present disclosure also includes a breast implant comprising a shell having a posterior side configured to face a chest cavity of a patient upon implantation and an anterior side opposite the posterior side, wherein the posterior side includes: a first surface having an average roughness ranging from about 2.0 µm to about 6.0 µm; at least one second surface having an average roughness greater than the average roughness of the first surface, wherein the at least one second surface is located on an upper portion of the posterior side for contacting an upper portion of the chest cavity of the patient upon implantation; and a flexible strap configured for attachment to an anatomical feature of the patient. The breast implant may include one or more other features of the breast implants and/or other implants discussed above or elsewhere herein.

The various examples provided herein, including the examples above, serve to illustrate various aspects of the present disclosure, and should not be interpreted as the only examples or embodiments contemplated herein. It is to be understood that the above examples and/or portions thereof may be combined and/or interchanged with one another. Additional examples, embodiments and advantages will be set forth in part in the description which follows, including variations and alternatives of the examples provided according to the general principles provided herein, which may be understood from the description and/or may be learned by practice of the disclosure based on the guidance herein.

BRIEF DESCRIPTION OF THE FIGURES

The accompanying drawings, which are incorporated in and constitute a part of this specification, illustrate various examples and together with the description, serve to explain the principles of the present disclosure. Any features of an embodiment or example described herein (e.g., device, method, etc.) may be combined with any other embodiment or example, and are encompassed by the present disclosure.

FIGS. 7A-7G show posterior surfaces of several exemplary implants, according to some aspects of the present disclosure.

FIG. 11 shows exemplary customization parameters of an implant, according to some aspects of the present disclosure.

DETAILED DESCRIPTION

Figure 1B:
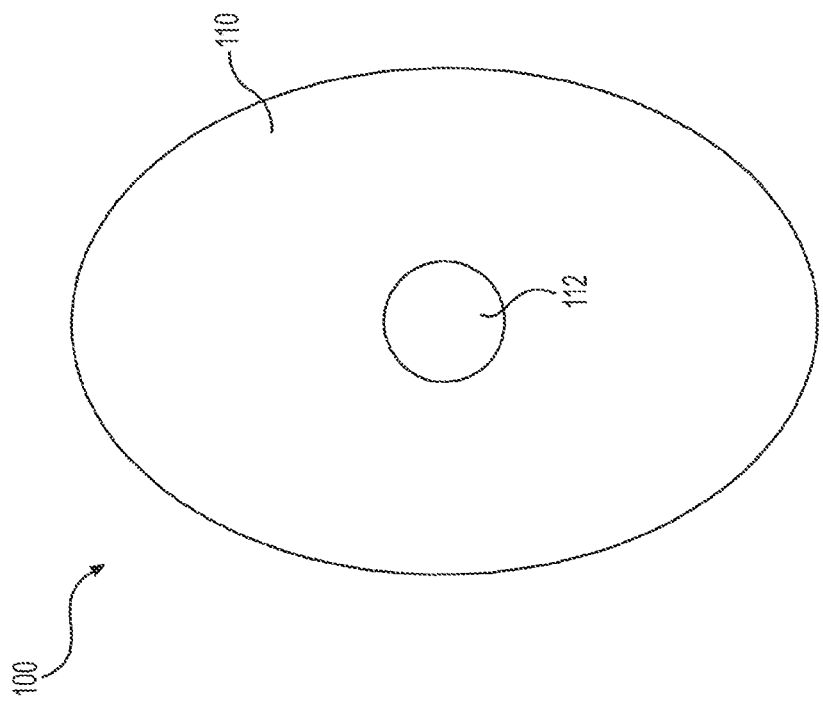
FIGS. 1A and 1B show an exemplary implant, according to some aspects of the present disclosure.

Aspects of the present disclosure are described in greater detail below. The terms and definitions as used and clarified herein are intended to represent the meaning within the present disclosure. The terms and definitions provided herein control, if in conflict with terms and/or definitions incorporated by reference.

The singular forms "a," "an," and "the" include plural reference unless the context dictates otherwise. The terms "approximately" and "about" refer to being nearly the same as a referenced number or value. As used herein, the terms "approximately" and "about" generally should be understood to encompass ±5% of a specified amount or value.

As used herein, the term "posterior" refers to the backside of a patient, and the term "anterior" refers to front of a patient. Thus, the posterior side of a breast implant is the side of the implant facing the chest wall, while the anterior side is the opposite side closest to the skin. Similarly, the posterior side of a gluteal or buttock implant is the side closest to the skin, and the anterior side is the opposite side facing the pelvis. As used herein, the term "proximal" refers to a direction or location closer to a patient (e.g., the posterior side of a breast implant closest to the chest wall), whereas the term "distal" refers to a direction or location farther from the patient (e.g., the anterior surface of a breast implant closest to the skin).

The present disclosure generally relates to medical implants, their features, and methods of producing and customizing such implants. Various aspects of the present disclosure may be used with and/or include one or more features disclosed in U.S. Provisional Application No. 62/313,218, entitled "Sensors for Implantable Medical Devices and Methods of Use Thereof," filed on Mar. 25, 2016; U.S. Provisional Application No. 62/318,402, entitled "Medical Imaging Systems, Devices, and Methods," filed on Apr. 5, 2016; U.S. Provisional Application No. 62/323,160, entitled "Minimally-Invasive Apparatus for the Implantation of Medical Devices and Methods of Use Thereof," filed on Apr. 15, 2016; U.S. Provisional Application No. 62/334,667, entitled "Implant Surface Technologies and Elements of Formation," filed on May 11, 2016; U.S. Application Publication No. 2015/0282926; U.S. Application Publication No. 2014/0081398; and/or U.S. Application Publication No. 2014/0078013.

Implantable medical devices having a substantially uniform or otherwise controlled surface topography and materials suitable for such devices are disclosed herein. For example, the implant surfaces disclosed herein may exhibit a consistent texture on at least a portion or all outer surfaces/sides of the implant. In some aspects, the implants disclosed herein may include uniform surface features on the order of nanometers to micrometers. Further disclosed herein are implants comprising portions with different surface textures or roughness characteristics. The implants herein may include one or more features or properties to assist in biocompatibility, fixation, positioning, tracking, and/or identification. Also disclosed herein are processes to manufacture such implants.

Although aspects of the present disclosure may be described in the context of a given type of medical implant, such as, for example, a breast prosthesis, embodiments of the present disclosure may be, and/or may be applied to, a variety of medical implants and instruments. Non-limiting examples include, e.g., coatings for electro-stimulation implants (e.g., pacemakers, spinal cord stimulators), drug delivery reservoirs, catheters, indwelling catheters, injection ports, drug delivery ports, inner and/or outer surfaces of gastric balloons, gastric bands, body contour implants such as gluteal, calf, testicular, and penile implants, etc.

Medical implants may be described or characterized by various parameters. For example, the surface of an implantable medical device may have a specified texture, hydrophobicity or hydrophilicity, and elasticity, among other physical and chemical properties. With respect to texture, for example, surface topography may be described by roughness, kurtosis, and/or skewness values, e.g., based on the shapes, sizes, and/or distribution of topographical projections (peaks) and recesses (valleys), discussed below According to some aspects of the present disclosure, it may be desirable to provide the outer surface of an implant with controlled physical and/or chemical characteristics, e.g., to assist in patient safety and/or comfort. Implants having controlled surface features may improve implant biocompatibility, and therefore improve clinical outcomes. Without intending to be bound by theory, it is believed that the implant surfaces prepared according to the present disclosure may help to reduce adverse physiological reactions, including cellular responses such as fibroblast activity, and/or may reduce immune response to implants that may lead to the formation of reactive tissue capsules around the implant (e.g., capsular contracture).

According to further aspects of the present disclosure, methods of manufacturing implant surfaces with consistent, controlled physical and/or chemical characteristics may be desired, e.g., to allow for reproducibility in implant manufacturing, and predictability and uniformity in implant surface characteristics. Moreover, the methods herein may produce implant surfaces with controlled physical and/or chemical characteristics, while also minimizing or eliminating extraneous particulate matter or other debris on the implant surfaces. This lack of debris on the surface may, for example, reduce or avoid irritation of patient tissue associated with the debris. Without intending to be bound by theory, it is believed that methods of preparing implant surfaces disclosed herein may allow for consistent, reproducible implants and implant surfaces having controlled physical and/or chemical properties, and may result in implant surfaces carrying little or no debris, such as salt particles or other abrasive particulate matter used in other surface texturizing methods. Further, for example, the implants having the physical and/or chemical surface characteristics disclosed herein may provide benefits in biocompatibility of the implants, leading to more stable thin capsules around the implants and/or less foreign body reaction.

Figure 1A:
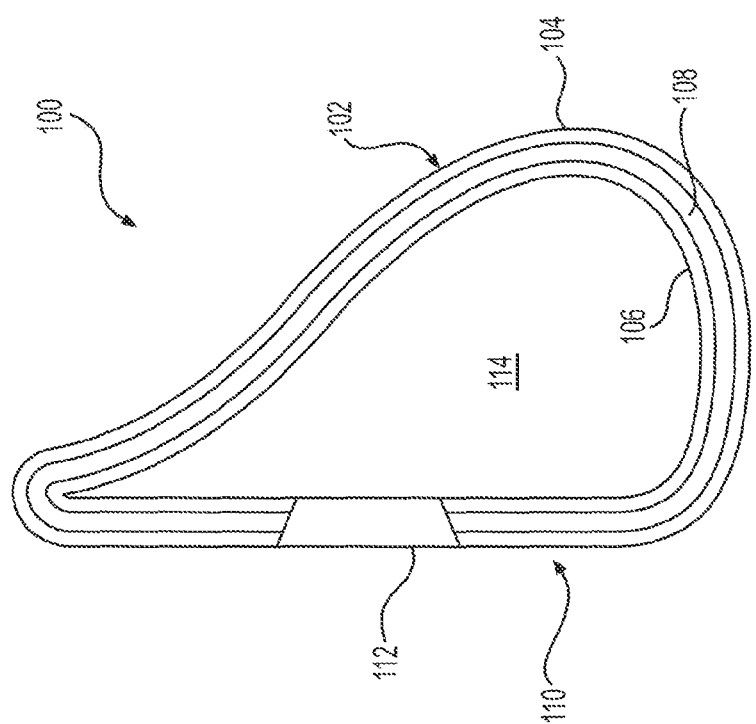

FIGS. 1A and 1B depict views of an exemplary implant 100, which may embody one or more aspects of the disclosure herein. FIG. 1A depicts a cross-sectional side view of implant 100. Implant 100 may have a shell 102 that encloses or surrounds a filling 114. Shell 102 may comprise a single-layer or may be multi-layered. As shown, for example, shell 102 may have an outer surface 104 and an inner surface 106. When the shell 102 comprises multiple layers, the shell 102 may include one or more layers 108 between the inner and outer surfaces 104, 106. Shell 102 may have a proximal or posterior side 110, which may comprise a patch 112 useful for introducing the filling 114 into the implant 100.

Implant 100 may have a variety of shapes and sizes suitable for implantation in the body. For example, implant 100 may be a breast implant having a size and shape suitable for implantation during a breast augmentation or reconstruction surgery. Shell 102 of implant 100 may be a single or multi-layered shell, made of one or more biocompatible materials suitable for the implant. For example, shell 102 may comprise a series of successive layers of silicone, which may be cross-linked or otherwise attached together. One or more layers of shell 102 may comprise, for example, one or more siloxane polymer elastomers. When the shell 102 comprises multiple layers, each layer may have the same or different compositions and/or elasticity characteristics. For example, polymer or copolymer dispersions with different viscosities may be used to prepare the layers of a multilayered shell 102.

Patch 112 of posterior side 110 may be a single or multilayered patch of a biocompatible material. For example, patch 112 may comprise silicone. In some embodiments, patch 112 may be contiguous with shell 102. In further embodiments, patch 112 may be a single- or multilayered patch (e.g., made of layers of a silicone dispersion) constructed separately from shell 102, and affixed to shell 102 via, for example, adhesion or vulcanization of patch 112 to implant 100. In some embodiments, patch 112 may cover an aperture in shell 102. In some embodiments, patch 112 may comprise a material or texture that is different from the texture of shell 102. In further embodiments, patch 112 may not be located on posterior side 110, and may instead be located on another side of implant 100. In yet further embodiments, implant 100 may not have a patch 112. The filling 114 of implant 100 may comprise any material or combination of materials suitable for an implant. For example, in a breast prosthesis, filling 114 may comprise a biocompatible liquid or gel filler material, such as a saline liquid or a silicone gel.

Reference will now be made to characteristics of surfaces of implants according to the present disclosure. While certain principles or features are described in the context of implant 100 as an example, the present disclosure is not limited to implants of the type illustrated in FIGS. 1A-1B. The concepts disclosed herein may be used for any suitable medical implants.

Implant surface texture may be at least partially characterized by deviations in the surface from a hypothetical, perfectly flat surface. Such deviations may be on a macro level, e.g., visible to the naked eye, and/or on a microscopic level, e.g., via a suitable analytical technique. Surface texture implicates a combination of features and materials that may contribute to the visual and/or tactile properties of a surface. As such, surface texture may be characterized by one or several parameters or dimensions such as roughness, skewness, kurtosis, peak and valley heights/depths, and/or the number of peaks per unit area.

"Roughness" in the present disclosure generally refers to the coarseness or unevenness of a surface, e.g., from projections/peaks, recesses/valleys, irregularities, and/or breaks in the surface. Roughness may be characterized, for example, by peaks and valleys that provide for a textured surface. If such variations in a surface are relatively large, then the surface may be characterized as "rougher" than a surface in which such variations are relatively small. Roughness of a surface may be described mathematically by an average roughness value $R_a$ and/or average root mean square roughness value $R_q$:

$$R_a = \frac{1}{l}\int_0^l |z(x)|dx \qquad \text{Equation 1}$$

$$R_q = \sqrt{\frac{1}{l}\int_0^l (z(x))^2 dx} \qquad \text{Equation 2}$$

where l is the surface length and z(x) is the surface profile along the x-axis. In three dimensions, the average roughness value $S_a$ and average root mean square roughness value $S_q$ may be determined as follows:

$$S_a = \frac{1}{A}\int\int_A |z(x,y)|dxdy \qquad \text{Equation 3}$$

$$S_q = \sqrt{\frac{1}{A}\int\int_A (z(x,y))^2 dxdy}$$  Equation 4 where A is the surface area and z(x,y) is the surface profile along the x-axis and y-axis. Roughness of a surface may be measured by, for example, using a profilometer, such as an optical 3D microscope, a contact profilometer, or a non-contact profilometer. The measurements may provide a two-dimensional and/or three-dimensional profile of the surface from which roughness may be quantified.

Kurtosis generally refers to a numerical characterization of the sharpness of the distribution of peak heights and valley depths of a surface, relative to a mean line of the surface. The kurtosis value of a surface may be calculated based on the measured surface roughness, e.g., via a profilometer. Kurtosis in two dimensions ($R_{ku}$) and three dimensions ($S_{ku}$) may be determined mathematically as follows:

$$R_{ku} = \frac{1}{R_q^4}\left(\frac{1}{l}\int_0^l (z(x))^4 dx\right)$$  Equation 5

$$S_{ku} = \frac{1}{S_q^4}\left(\frac{1}{A}\int\int_A (z(x,y))^4 dxdy\right)$$  Equation 6

Figure 2:
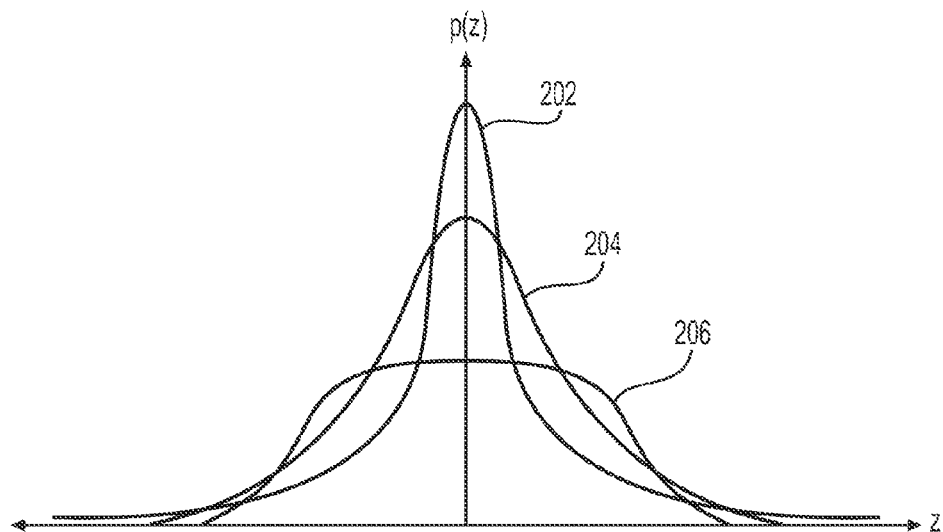
FIG. 2 is a schematic representation of different kurtosis values.

FIG. 2 depicts three exemplary curves to illustrate the kurtosis values of three different surfaces. If the surface heights and depths of peaks and valleys, respectively, of a textured surface are normally distributed (e.g., forming the shape of a bell such as curve 204), then the kurtosis value is 3 or close to 3. A kurtosis value of 3 describes a surface having a Gaussian distribution of peak heights and valley depths. A textured surface having peaks and valleys that exhibit more deviations from the surface's mean peak heights and valley depths may generally have a kurtosis value less than 3, as represented by curve 206. For example, a textured surface having few, varied peaks and/or the appearance of a series of rolling hills (e.g., a "bumpy" surface profile), may have a kurtosis value less than 3. A textured surface having more centrally distributed peak heights and valley depths, i.e., less variation and more uniformity in peak heights and valley depths, as represented by curve 202, may have a kurtosis value that is greater or considerably greater than 3. Within the context of this disclosure, the term "kurtosis" refers to the kurtosis value normalized about 3, in which a value of 3 indicates a surface having a Gaussian distribution of peak heights and valley depths.

Kurtosis values may be adjusted in some cases (e.g., by certain instruments used to measure surface characteristics) so that a value of 0 describes a normal distribution of peak heights and valley depths, instead of a value of 3. This may be done by calculating the kurtosis value (e.g., using Equation 5 or Equation 6), and then subtracting 3 in order to normalize the value about 0. Using this nomenclature, a value of 0 indicates a surface having a Gaussian distribution of peak heights and valley depths, a value less than 0 indicates a surface having peak heights and valley depths exhibiting more deviations from mean peak heights and valley depths, and a value greater than 0 indicates a surface having more centrally distributed peak heights and valley depths, i.e., more uniformity in peak height and valley depth. Within the context of this disclosure, the term "normalized kurtosis" refers to the kurtosis value normalized about 0, in which a value of 0 indicates a surface having a Gaussian distribution of peak heights and valley depths.

In the present disclosure, the term "skewness" may be used to describe a numerical characterization of a symmetry or asymmetry/irregularity of height distribution of a surface, such as whether peaks or valleys predominate as compared to a mean line of the surface. The skewness value of a surface may be calculated based on the measured surface roughness, e.g., via a profilometer. Skewness in two dimensions ($R_{sk}$) and three dimensions ($S_{sk}$) may be determined mathematically as follows:

$$R_{sk} = \frac{1}{R_q^3}\left(\frac{1}{l}\int_0^l (z(x))^3 dx\right)$$  Equation 7

$$S_{sk} = \frac{1}{S_q^3}\left(\frac{1}{A}\int\int_A (z(x,y))^3 dxdy\right)$$  Equation 8

A skewness value of 0 indicates that neither peaks nor valleys predominate in a surface. A positive skewness may indicate a predominance of peaks over a mean line of the surface. A negative skewness, in contrast, may indicate a predominance of valleys. For example, if the average height of peaks is equal to the average depth of valleys across the surface, then the skewness of the surface is 0.

In some aspects of the present disclosure, the implants may have surface features with size dimensions on the order of nanometers and/or microns. For example, the surface features (e.g., peak heights and/or valley depths) may have dimensions ranging from about 5 µm to about 100 µm, such as from about 10 µm to about 100 µm, from about 5 µm to about 50 µm, from about 5 µm to about 25 µm, from about 10 µm to about 25 µm, from about 10 µm to about 18 µm, from about 10 µm to about 12 µm, from about 15 µm to about 35 µm, from about 10 µm to about 26 µm, or from about 10 µm to about 15 µm. In some examples, the implant surface may have an average peak height and/or an average valley depth of about 5 µm, about 10 µm, about 12 µm, about 15 µm, about 18 about 20 µm, about 22 µm, about 25 µm, about 26 µm, about 28 µm, about 30 µm, about 32 µm, about 35 µm, about 40 µm, or about 50 µm, See also Table 1 below. The average peak height may be the same or different than the average valley depth.

Figure 3:
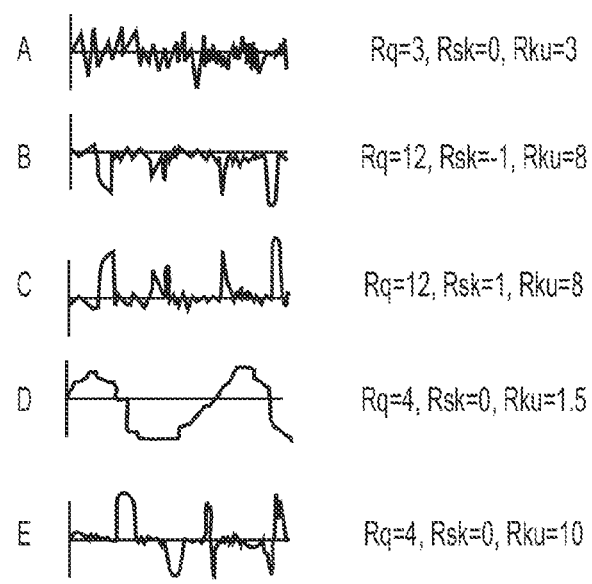
FIG. 3 illustrates exemplary surfaces and corresponding surface characteristics, according to some aspects of the present disclosure.

FIG. 3 depicts two-dimensional cross-sectional characterizations of five exemplary surfaces (A-E) with different surface textures, meaning that each surface has a different combination of surface characteristics, e.g., roughness (as measured by the root mean square height of surface roughness) ($R_q$), skewness ($R_{sk}$), and kurtosis ($R_{ku}$). For each surface, a horizontal line indicates the mean line of the surface profile, wherein peaks are above the mean line (the height of a peak being measured from the mean line to the highest point of the peak), and valleys are below the mean line (the depth of a valley being measured from the mean line to the lowest point of the valley).

For example, surface A has a roughness value of 3 µm (indicating a relatively smooth surface), a skewness value of 0 (a predominance of neither peaks nor valleys), and a kurtosis value of 3 (a normal distribution of peak and valley heights). Surface B has a roughness value of 12 µm (indicating a relatively rough surface), a skewness value of −1 (indicating a predominance of valleys under the mean surface line), and a kurtosis value of 8 (indicating that the valleys are "spiky" or sharper than a Gaussian surface).

Surface C has roughness and kurtosis values equivalent to those of surface B, but with a skewness of 1, indicating a predominance of peaks, instead of valleys, over the mean surface line. Surface D has a roughness value of 4 μm (indicating a somewhat smooth surface), a skewness value of 0 (indicating that neither peaks nor valleys predominate), and a kurtosis value of 1.5, indicating a less spiky and more rolling surface texture. Surface E has roughness and skewness values equivalent to those of surface D, but with a kurtosis of 10, indicating that the surface comprises sharp peaks and valleys as opposed to rolling bumps.

As illustrated by FIG. 3, two surfaces having the same roughness value may not have other surface characteristics that are the same. For example, surfaces B and C have the same roughness value but different surface profiles as shown and as indicated by the skewness value. Similarly, surfaces D and E have the same roughness value but different surface profiles as shown and as indicated by the kurtosis value. The implants herein may have a controlled surface texture with a combination of surface characteristics (not just a given surface roughness) that may provide benefits for implantation in a patient, as discussed herein.

Implant surfaces according to some aspects of the present disclosure may have a kurtosis value ($S_{ku}$) between about 2.5 and about 3.0 or greater than 3.0. For example, the kurtosis value may range from about 3.0 to about 7.0, such as from about 3.0 to about 5.0, from about 3.0 to about 4.0, from about 3.5 to about 5.0, from about 3.0 to about 5.5, from about 3.5 to about 4.5, or from about 4.0 to about 7.0. In some examples, the kurtosis value of the outermost surface(s) of an implant (the surface(s) of the implant in contact with bodily tissues) may range from about 3.0 to about 5.0, e.g., a kurtosis value of about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, or about 5.0. In at least one example, a portion of, or an entirety of, the outermost surface of the implant may have a kurtosis value of 3.5±0.5. In some embodiments, implant surfaces according to the present disclosure may have a kurtosis value of approximately 3.0, e.g., representing a relatively equal distribution of peaks and valleys with similar scale heights. In at least one example, a portion of, or an entirety of, the outermost surface of the implant may have a kurtosis value of 3.1±0.4. In some embodiments, at least a portion of the implant surface may have a kurtosis value greater than 3.0, e.g., a kurtosis value of 4.0±0.5, or 4.5±0.5. In at least one example, a portion of, or an entirety of, the outermost surface of the implant may have a kurtosis value ranging from about 4.7 to about 4.8. In at least one example, a portion of, or an entirety of, the outermost surface of the implant may have a kurtosis value ranging from about 4.5 to about 4.6.

Further, implant surfaces according to the present disclosure may have a skewness value ($S_{sk}$) ranging from about −0.2 to about 2.0, such as from 0 to about 0.4, from about 0.2 to about 0.6, from about 0.5 to about 1, from about 0.6 to about 2.0, or from about 0.4 to about 0.8, e.g., a skewness value of about 0.1, about 0.2, about 0.3, about 0.4, about 0.5, about 0.6, about 0.7, about 0.8, about 0.9, or about 1.0. In some aspects, the skewness value of a surface may be approximately zero or a positive value, e.g., a slightly positive value such as 0.1, 0.2, 0.3, 0.4, or 0.5. In at least one example, a portion of, or an entirety of, the outermost surface of the implant may have a skewness value ranging from about 0.4 to about 0.5. In at least one example, a portion of, or an entirety of, the outermost surface of the implant may have a skewness value ranging from 0 to about 0.3. In at least one example, a portion of, or an entirety of, the outermost surface of the implant may have a skewness value ranging from about 0.4 to about 0.5. In at least one example, a portion of, or an entirety of, the outermost surface of the implant may have a skewness value ranging from about 0.8 to about 0.9.

Further, in some aspects, implant surfaces of the present disclosure may have an average roughness ($S_a$) ranging from about 2 μm to about 6 μm, such as from about 2.2 μm to about 5.8 μm, from about 2.5 μm to about 5.5 μm, from about 3.0 μm to about 5.0 μm, or from about 3.5 μm to about 4.5 μm. For example, the average roughness ($S_a$) of an implant surface may be about 2.5 μm, about 3.0 μm, about 3.5 μm, about 4.0 μm, about 4.5 μm, about 5.0 μm, about 5.5 μm, or about 6.0 μm. In at least one example, a portion of, or an entirety of, the outermost surface of the implant may have an average roughness ($S_a$) of about 3.1 μm or about 3.4 μm.

In some examples of the present disclosure, the implant surface may have an average roughness ($R_a$) ranging from about 2 μm to about 20 μm, such as from about 4 μm to about 18 μm, from about 5 μm to about 15 μm, from about 16 μm to about 18 μm, or from about 10 μm to about 20 μm. In at least one example, a portion of, or an entirety of, the outermost surface of the implant may have an average roughness ($R_a$) of 3.9±0.5 μm.

In some embodiments of the present disclosure, the implant surface may have a density of contact points in the range of about 2,500 peaks/cm² to about 65,000 peaks/cm², such as a density of contact points ranging from about 5,000 peaks/cm² to about 15,000 peaks/cm², from about 5,000 peaks/cm² to about 10,000 peaks/cm², from about 10,000 peaks/cm² to about 20,000 peaks/cm², or from about 10,000 peaks/cm² to about 15,000 peaks/cm², from about 20,000 peaks/cm² to about 65,000 peaks/cm², from about 20,000 peaks/cm² to about 60,000 peaks/cm², from about 30,000 peaks/cm² to about 60,000 peaks/cm², from about 12,000 peaks/cm² to about 50,000 peaks/cm², from about 30,000 peaks/cm² to about 50,000 peaks/cm², from about 45,000 peaks/cm² to about 55,000 peaks/cm², from about 40,000 peaks/cm² to about 50,000 peaks/cm², from about 40,000 peaks/cm² to about 45,000 peaks/cm², or from about 45,000 peaks/cm² to about 50,000 peaks/cm². For example, the surface may have about 5,000 peaks/cm², about 7,500 peaks/cm², about 8,000 peaks/cm², about 8,500 peaks/cm², about 9,000 peaks/cm², about 9,500 peaks/cm², about 10,000 peaks/cm², about 12,500 peaks/cm², about 15,000 peaks/cm², about 17,500 peaks/cm², about 20,000 peaks/cm², about 25,000 peaks/cm², about 30,000 peaks/cm², about 35,000 peaks/cm², about 40,000 peaks/cm², about 45,000 peaks/cm², about 50,000 peaks/cm², about 55,000 peaks/cm², about 60,000 peaks/cm², or about 65,000 peaks/cm². The density of contact points of an implant surface may be measured using, for example, a 3D non-contact microscope.

Other measurements may also be used to characterize implant surfaces according to the present disclosure, such as average peak and valley heights, and the number of peaks per unit area. Table 1 shows ranges of exemplary roughness, kurtosis, skewness, and other values that may characterize the surface texture of an implant (e.g., surface characteristics within a given sampling area, which may be the entire posterior and/or anterior implant surface or a portion thereof) according to some aspects of the present disclosure.

As discussed above, peak height and valley depth are distances measured relative to a mean line of the surface profile. The maximum peak height ($S_p$) refers to the greatest distance above the mean line, and the maximum valley depth ($S_v$) refers to the greatest distance below the mean line, both peak heights and valley depths being absolute values. The total height of the surface profile refers to the combined value of the maximum peak height and maximum valley depth ($S_p+S_v$). The mean height of the surface profile refers to the average of the combined peak heights and valley depths across the surface.

TABLE 1

| Surface Characteristic | Exemplary Range |
|---|---|
| Avg. Roughness ($S_a$) | 4.0 μm ± 2 μm |
| Avg. Root Mean Square Roughness ($S_q$) | 4.5 μm ± 2 μm |
| Skewness ($S_{sk}$) | 0.6 ± 0.4 |
| Kurtosis ($S_{ku}$) | 3.0 to 5.0 |
| Maximum Peak Height ($S_p$) | 14 μm ± 2 μm |
| Maximum Valley Depth ($S_v$) | 12 μm ± 2 μm |
| Total Height of Surface Profile (max. peak height + max. valley depth) | 25 μm ± 4 μm |
| Mean Height of Surface Profile (average of peak heights + valley depths) | 13 μm ± 2 μm |
| Density of Contact Points (peaks/cm²) | 20,000 to 60,000 |

At least one exemplary implant surface of the present disclosure may exhibit, for example, an average roughness ($S_a$) of 3.1 μm, a skewness ($S_{sk}$) of 0.89, and a kurtosis ($S_{ku}$) ranging from 4.7 to 4.8. Another exemplary implant surface of the present disclosure may exhibit, for example, an average roughness ($S_a$) of 3.4 μm, a skewness ($S_{sk}$) of 0.8, and a kurtosis ($S_{ku}$) ranging from 4.5 to 4.6. Ina further example, the implant may comprise an outer surface having an average roughness ($R_a$) of 3.9±0.5 μm, a skewness ($S_{sk}$) of 0.4±0.1, and a kurtosis ($S_{ku}$) of 3.1±0.4. In yet another example, the implant may comprise an outer surface having an average roughness ($R_a$) of 4.0±0.4 μm, a skewness ($S_{sk}$) of 0.1±0.2, and a kurtosis ($S_{ku}$) of 2.6±0.2.

The present disclosure encompasses surfaces that exhibit other exemplary ranges of these properties as well. For example, embodiments of the present disclosure may exhibit an average roughness ($S_a$) of 2.5 μm±1.0 μm or 6.0 μm±2.0 μm and/or a root mean square roughness ($S_q$) of 2.5 μm±1.0 μm or 6 μm±2.0 μm. Further, embodiments of the present disclosure may exhibit a skewness ($S_{sk}$) of, for example, 0.6±1.2, and/or a kurtosis ($S_{ku}$) ranging from 2.5 to 6.0. Implant surfaces of the present disclosure may exhibit peak heights ($S_p$) of 25 μm±15 μm and/or valley depths ($S_v$) of 10 μm±5 μm or 20 μm±5 μm. In some examples, implant surfaces of the present disclosure may exhibit a contact point density ranging from 20,000 peaks cm² to 60,000 peaks/cm², such as from 30,000 peaks/cm² to 55,000 peaks/cm², or from 40,000 peaks/cm² to 50,000 peaks/cm². In other examples, the surfaces herein may have an average roughness (Sa) of 4.0 μm±1.0 μm, a skewness ($S_{sk}$) of 0.4±0.2, a kurtosis ($S_{ku}$) of 3.1±0.4, a maximum peak height of 14 μm±2.0 μm, an average peak height of 13 μm±2.0 μm, a valley depth of 12 μm±2.0 μm, and a contact point density ranging from 40,000 to 50,000 peaks/cm². Further, the present disclosure contemplates that embodiments may have combinations of properties exhibiting any of these exemplary ranges, optionally in combination with properties exhibiting any of the exemplary ranges disclosed in Table 1.

Implants may be prepared as discussed herein to achieve a combination of desired surface characteristics.

Figure 4:
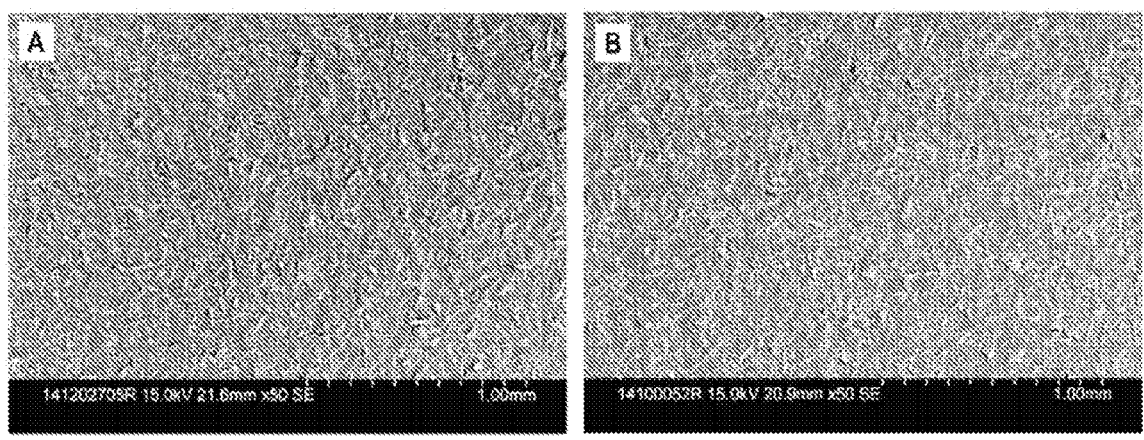
FIG. 4 shows scanning electron microscopy (SEM) images of two exemplary surfaces, in accordance with some aspects of the present disclosure.

FIG. 4 depicts images obtained by scanning electron microscopy (SEM) of two exemplary texturized silicone samples prepared according to the present disclosure, whose surfaces exhibit the properties described above. The surfaces were sputter-coated with gold-palladium and scanned using an SEM Hitachi 3700N.

Relative hydrophobicity of an implant surface may also improve biocompatibility of an implant surface. An implant (e.g., a breast implant) having a relatively hydrophilic surface may adhere to water-rich tissue and cause undesirable stiction, or static friction, that must be overcome to enable relative movement between the implant surface and the tissue. In contrast, a relatively hydrophobic surface, when in contact with water-rich living tissue (e.g., tissue at the front of a patient's chest cavity), may generate less friction against the tissue. Hydrophobicity and hydrophilicity generally may be described in terms of the "wettability" of a surface, or the affinity of a liquid towards the surface.

Measurements of contact angle (also referred to as wetting angle) may provide an indication of the hydrophobicity and wettability of a surface. The contact angle of a surface is measured as the angle between the surface and the edges of a liquid droplet (e.g., water droplet) on the surface. Thus, hydrophobic surfaces generally have contact angles greater than 90°, whereas hydrophilic surfaces generally have contact angles less than 90°.

Wettability of a surface may be affected by the chemical composition and/or physical properties of the surface, such as topography, e.g., roughness. For example, increasing surface roughness may correspond to increasing discrete points of contact between the surface and a water droplet in contact with the surface. This in turn may allow for air pockets between the points of contact of the surface and the water droplet, e.g., increasing the relative hydrophobicity of the surface. However, as discussed herein, excessive roughness of an implant surface may cause tissue encapsulation and capsular contraction. Therefore, implant surfaces according to some aspects of the present disclosure may exhibit relative hydrophobicity without excessive roughness. Accordingly, implant surfaces according to some aspects of the present disclosure may exhibit a contact angle between about 90° and about 150°, such as between about 100° and about 130°, between about 110° and about 130°, between about 115° and about 125°, e.g., a contact angle of about 110°, about 115°, about 120°, or about 125°.

Figure 6:
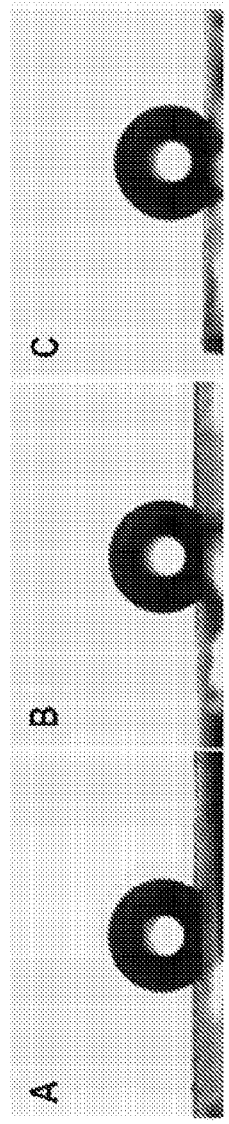
FIG. 6 shows contact angle measurements for three exemplary surfaces, in accordance with some aspects of the present disclosure.

FIG. 6 depicts images of three exemplary textured surface samples prepared according to the present disclosure during contact angle measurements (panels A, B, and C), each with a drop of water in contact with the surface, using a goniometer (ramé-hart CAM 200 system, ramé-hart instrument co, USA). The beaded appearance to the water droplets indicates that the surfaces are relatively hydrophobic (contact angles >90°). See also Example 3, below.

As mentioned above, the surface characteristics described herein may be incorporated into the outermost surface of a medical implant. For example, outer surface 104 of implant shell 102 may have a surface texture as described herein. Additionally or alternatively, one or more surfaces of an implant shell patch, such as inner and/or outer surfaces of patch 112 of implant 100, may have a surface texture as described herein. In some embodiments, surfaces other than the outermost surface of an implant may have a surface texture as described herein. For example, an inner surface of an implant shell, such as inner surface 106 of shell 102, may have a surface texture as described herein. Such a texturized inner surface may have improved interactions (e.g., increased adhesion or grip) with one or more other components of the implant, such as an inner component of the implant (e.g., filling 114). For example, a texturized inner surface (e.g., inner surface 106) may exhibit increased adhesion to an inner component of the implant (e.g., filling 114), thus preventing or reducing potential separation of the inner component from the texturized inner surface during manufacturing, sterilization, and/or implantation, and/or throughout the lifespan of the implant.

Implants according to the present disclosure may include areas having different surface characteristics. For example, the outermost surface of an implant (e.g., outer surface 104 of implant 100 in FIGS. 1A-1B) may have different surface characteristics than an inside surface of the implant (e.g., inner surface 106). Methods of texturizing inner surfaces of shells are discussed below.

In some embodiments, the implant surface may be prepared such that one or more select areas of the surface has different surface characteristics than other portions or a remainder of the surface. For example, the surface may include one or more areas having a higher average roughness value than other portions of the implant surface. When such areas with increased roughness are on the outermost surface of the implant, for example, they may provide a modest increase in implant immobility by increasing friction between the implant and patient tissue. Further, for example, select areas of the implant surface may be prepared by higher or lower kurtosis and/or skewness values, as compared to other portions of the implant surface.

Referring to FIGS. 1A-1B, for example, a portion of outer surface 104 of implant 100 may have different average roughness values than other portions of outer surface 104. For example, the posterior side 110 of implant 100 may comprise one or more discrete areas or regions having a higher average surface roughness. Such rougher portions of outer surface 104 may provide for increased friction with the surrounding tissue, and thus may help to restrict migration of the implant. In some aspects of the present disclosure, such rougher portions may avoid having a rougher (and potentially less biocompatible) surface on the entirety or the majority of the implant. In some aspects, for example, the patch 112 may have a higher roughness value than the remaining outer surface 104.

FIGS. 7A-7G depict several exemplary configurations or patterns of surface features of an implant useful for restricting movement of the implant after implantation. The configuration of the surfaces and/or the location of the surfaces relative to the surrounding tissue after implantation may limit or prevent movement of the implant relative to those tissues. For example, surfaces having a higher roughness may provide for increased friction against patient tissue that restricts movement of the implant. The combination of different surface textures may prevent the implant from rotating or otherwise migrating from its proper position when implanted. For example, the posterior and/or anterior side of an implant may include a plurality of surfaces of various sizes and shapes, e.g., forming a pattern of surface features for restricting movement of the implant.

Referring to the implant 100 of FIGS. 1A-1B, for example, the outer surface 104 of the implant 100 may have different surface textures, e.g., such that the outer surface 104 includes a combination of two or more surfaces have different surface textures. In at least one example, an upper portion of the posterior side 110 of the implant 100 may be configured to create friction against the tissue of a patient's upper chest cavity when implanted, in order to restrict movement of the implant 100. While FIGS. 7A-7G refer to the outer surface 104 of the posterior side 110 of the implant 100 of FIGS. 1A and 1B, the configurations depicted in FIGS. 7A-7G and discussed herein are not limited to a breast implant, or to the posterior side of a medical implant. The combinations of surface features disclosed herein may be used on any surface (e.g., anterior and/or posterior surface) of any implant (e.g., breast implant, gluteal implant, calf implant, or other implant).

In FIGS. 7A-7G, each of the shaded areas (e.g., 702, 708, 710, 712, 714, and 716, as well as the outer surface of patch 112) represents a surface (a portion of the outer surface 104 of the shell 102) having a particular surface texture or set of surface characteristics. Each surface 702, 708, 710, 712, 714, 716, and 112 may have the same or different surface texture than any other surface. In some aspects of the present disclosure, the implant may include one or more discrete surfaces having a higher surface roughness than an adjacent surface of the implant. In some aspects, the implant may include one or more discrete surfaces having a lower surface roughness than an adjacent surface of the implant.

For example, one or more of the darker-shaded surfaces 708, 710, 712, 714, and/or 716 may have a surface texture different than the surface texture of the lighter-shaded surface 702. Additionally or alternatively, each darker-shaded surface may have a surface texture that is the same or different than the surface texture of at least one other darker-shaded surface. The surfaces may have any suitable size and shape. For example, the surfaces may be curved (e.g., circular, oval, arched, or annular/ring-shaped), or geometric (e.g., triangular, square, rectangular, rhomboid, or trapezoidal), among other possible shapes. The implant may comprise a plurality of surfaces forming a symmetrical pattern, as shown, or a pattern that is not symmetrical.

For example, FIG. 7A depicts the posterior side 110 of implant 100 having a first surface 702 that may have a first surface texture including a set of surface characteristics of roughness, skewness, kurtosis, peak height, valley depth, and/or contact point density as disclosed herein. FIG. 7A also depicts patch 112 on outer surface 104, which may exhibit surface characteristics that are the same as those of the first surface 702, or that are different from those of first surface 702. In some embodiments, for example, patch 112 may exhibit a higher average roughness value than that of the first surface 702.

Additional surfaces of the posterior side 110 implant 100 (surfaces 708, 710, and 712) may also have differing surface characteristics from the first surface 702. For example, a surface 708 having the shape of a ring surrounding the patch 112 and centered on the posterior side 110 may exhibit one or more surface characteristics that differ from the surface characteristic(s) of the first surface 702. Similarly, a surface 710 having a generally arched shape near the upper edge of the posterior side 110, and/or one or more generally circular surfaces 712. As shown, the arched surface 710 has a center of curvature at or proximate the center of the posterior side 110, however other locations and orientations are also contemplated herein. As shown, the different surfaces are arranged such that the posterior side 110 has an axis of symmetry (e.g., an axis through the center of the patch 112, equidistant from the two circular surfaces 712). One or more of these surfaces 708, 710, and/or 712 may, in some embodiments, have a higher roughness value than that of the first surface 702, and/or may differ with regard to other surface characteristics (e.g., skewness, kurtosis, peak height, valley depth, and/or contact point density). That is, the surfaces 708, 710, and/or 712 may have a different surface texture than the surface texture of the surrounding surface 702.

As mentioned above, such rougher portions of the implant may advantageously provide increased friction at certain areas of contact between the implant and patient tissue. For example, the surface 710 having an arched shape may provide increased friction between the upper portion of the posterior side 110 of implant 100 and the upper portion of the patient's chest cavity. This friction may inhibit rotation and/or migration of the implant, and/or may reduce the risk of separation between the implant and the patient's chest cavity. Further, while such rougher surfaces may comprise the majority of, or all of, the posterior side 110 of the implant 100, they need not do so. Rougher surfaces that comprise only parts of the posterior side 110 of the implant 100 (e.g., as illustrated in FIGS. 7A-7G) may advantageously restrict movement of the implant 100 without substantial tissue irritation, e.g., due to friction between a rough implant surface and patient tissue.

FIGS. 7B-7G depict other exemplary combinations of surfaces in various shapes and sizes, including a first surface 702 and one or more other surfaces that may exhibit one or more surface characteristics that are the same as or different than those of the first surface 702. Each of FIGS. 7B-7G includes an arched surface 710 and a ring-shaped surface 708 of the same size and having the same location as shown in FIG. 7A, although these surfaces may not be included in other examples. FIG. 7B also depicts a second, smaller arched surface 714 radially inward of, and spaced apart from, the larger arched surface 710. Each of the arched surfaces 710, 714, independently may exhibit surface characteristics different from first surface 702. The two arched surfaces 710, 714 are located on the upper portion of the posterior side 110 of the implant 100, such that the surfaces 710, 714 contact an upper portion of the patient's chest cavity when implanted. FIG. 7B also illustrates a surface 712 having a generally circular shape opposite the arched surfaces 710, 714, proximate the lower edge of the posterior side 110 of the implant 100. The three surfaces 710, 712, 714 may be aligned such that the posterior side 110 has an axis of symmetry as shown.

FIG. 7C depicts yet another exemplary implant surface including three circular surfaces 712, as compared to the two circular surfaces 712 depicted in FIG. 7A. The three circular surfaces 712 may have the same surface texture, or a different surface textures than one another. The three circular surfaces 712 all may have the same or substantially the same size (as shown in FIG. 7C), or one of the circular surfaces 712 may be larger or smaller than at least one of the other circular surfaces 712. Further, in some examples, one of the surfaces 712 may have a different shape than at least one of the other areas, e.g., a generally oval shape, arched shape, geometric shape, or any other shape.

FIG. 7D depicts a second arched surface 716 located on the lower portion of the posterior side 110 of the implant mirroring the arched surface 710 located on the upper portion of the posterior side 110. The ends the two arched surfaces 710, 716 may be close together, forming a nearly annular surface radially outward of the patch 112, which may have one or more surface characteristics that are different from the surface characteristics of the first surface 702. FIGS. 7E, 7F, and 7G depict additional variations on the placement, size, and shape of various surfaces (e.g., surfaces 708, 710, 712, and 714 discussed in reference to FIGS. 7A-7D) of the posterior side 110 of the implant 100 that may exhibit surface textures different from the surface characteristics of the first surface 702.

In some examples, the implant 100 may include more or fewer discrete surfaces than those illustrated in FIGS. 7A-7G. For example, the posterior side 110 of the implant 100 may have a configuration similar to any of FIGS. 7A-7G, further comprising a plurality of smaller, discrete surfaces distributed across the posterior surface 110. Additional configurations are likewise contemplated herein.

In some examples, the outer surface of the implant may include information useful in identifying and/or characterizing the implant. As shown in FIGS. 7A-7G, for example, the outer surface 104 may include one or more labels 706. For example, the label 706 may comprise text (e.g., letters, words, numbers, signs, and/or symbols) imprinted into a portion of the outer surface 104, or may comprise a separate material adhered or otherwise affixed to a portion of the outer surface 104. Such a label 706 may, for example, be imprinted into or embossed into the outer surface 104, and may include identification markings (e.g., manufacturer, model number, size dimensions, date of manufacture, etc.) or any other information useful for identifying the implant 100. The label(s) 706 may be located on any suitable portion of the implant 100, such as the first surface 702 and/or another surface such as patch 112, any of surfaces 708, 710, 712, or 714, or any other area of outer surface 104.

While FIGS. 7A-7G depict several exemplary surface configurations or patterns, one of ordinary skill in the art will understand that many other configurations are possible and may be appropriate for a given implant based on the size, shape, and/or orientation of the implant relative to different tissues when implanted. The number, size, shape, and location of such surfaces of the implant may be tailored according to the needs of a specific patient and/or the type of implant.

The different surface textures may be distributed across the implant surface to assist in restricting or preventing movement of the implant in one or more directions relative to the surrounding patient tissue (e.g., upwards movement, downwards movement, side-to-side movement, and/or rotation of the implant within the patient). In at least one example, the posterior and/or anterior surface of the implant may include at least one first surface having a first surface texture and at least one second surface having a second surface texture different than the first surface texture. For example, the second surface(s) may have an average roughness greater than the average roughness of the first surface(s).

The surfaces may be integral portions of the implant (e.g., an integral part of the shell or other outermost surface of the implant) or may be defined by a material coupled to the implant surface. For example, one or more of the surfaces 708, 710, 712, 714, and/or 716 of FIGS. 7A-7G may be defined by the outer surface of a tab attached to the outer surface of the implant. Each surface may have the same chemical composition or a different chemical composition than another portion of the implant surface. Referring to FIG. 7A, in one example, all of surfaces 708, 710, and 712 may be integral portions of the shell 102 of the implant 100, having the same chemical composition. In another example, surface 708 may be an integral portion of the shell 102, while surfaces 710 and 712 are defined by tabs coupled to the surface having the same chemical composition than the shell 102. In yet another example, each surface 708, 710, and 712 may be defined by a tab having a different chemical composition than the shell 102. Methods of preparing implants having different surface textures as integral portions of the implant are discussed below. Tabs also are discussed below.

Surface characteristics described herein may be incorporated into a variety of medical implants. Any suitable biocompatible material may be used for the implant surface, including, e.g., biocompatible polymers and/or copolymers. The material may be rigid, semi-rigid, or flexible, depending on the desired characteristics of the implant. For example, some implants such as pacemakers and other electro-simulation implants may have portions that are rigid or semi-rigid, whereas other implants such as breast implants or gluteal implants may be flexible.

In some embodiments, the surface characteristics described herein may be incorporated into breast implants having a flexible shell formed of a biocompatible polymer or copolymer, such as an elastomer. Exemplary materials include, but are not limited to, silicone materials. For example, the shell may be formed of one or more siloxane polymer elastomers or a siloxane polymer elastomer mixture. The composition of the silicone material may provide a high strength barrier and/or a higher elongation per unit force. In some embodiments, the composition of the silicone material may provide a barrier to prevent diffusion of a filling material from inside of the implant. For example, the silicone material may comprise a silicone elastomer comprising a polysiloxane backbone and having a minimum mole percentage of 10% of a substituted or pendant chemical group that retards permeation of silicone through the layer. In some examples, the silicone elastomer may be a polydimethylsiloxane and the pendant chemical group may be one of a phenyl or a fluorine group.

In some embodiments, the shell may be formed with one or more siloxane polymer elastomers having a viscosity suitable for providing a high strength barrier, and another siloxane polymer elastomer having a viscosity suitable for providing a higher elongation per unit force. In some embodiments, the shell may be formed by layers of each of these siloxane polymer elastomers with different viscosities, so as to create a shell having both a high strength barrier and/or a barrier to prevent diffusion of filling material, and a higher elongation per unit force.

In some embodiments, the shell may provide for at least +200% elongation as compared to other silicone materials used in medical implants, when measured using a tensile testing system (e.g., an Instron® static tensile testing system having a charged cell of 50 N). For example, some shells of the present disclosure may exhibit elongation values ranging from about 450% to about 750%, such as from about 500% to about 750%, from about 600% to about 750%, or from about 650% to about 750%. The elongation value may be measured according to standard ISO 37 of the International Organization for Standardization. Additionally or alternatively, the shell breaking strength (ultimate breaking force) of shells according to the present disclosure may range from about 11.0 N to about 45.0 N, such as from about 15.0 N to about 40.0 N, from about 20.0 N to about 30.0 N, or from about 25.0 N to about 35.0 N. The shell breaking strength may be measured according to standard ASTM F703-07. In some aspects of the present disclosure, the tear strength of the shell may range from about 8.0 N to about 18.0 N, such as from about 10.0 N to about 15.0 N, or from about 15.0 N to about 20.0 N. The tear strength may be measured according to standard ISO 34-1:2004, Method C. A silicone shell according to the present disclosure, in combination with an appropriate filling material, may allow an implant to be elongated, compacted, and loaded into introducer devices more efficiently, e.g., without compromising the integrity of the implant through rupture of the shell, leakage of filling material, loss of implant shape, and/or separation of filling material from the inner wall of the shell.

Some implants according to the present disclosure may comprise a filling material, such as a liquid or gel. For example, the filling material may allow the implant to more closely simulate tissue, e.g., by temporarily deforming in response to pressure or due to gravity. Any of the features of the gravity-sensitive implants disclosed in U.S. Publication No. 2015/0282926, incorporated by reference herein, may be used in the present disclosure. In some examples, the implant may be a breast prosthesis comprising a shell that encloses a biocompatible liquid such as saline, or a biocompatible gel such as a silicone gel. In such embodiments, suitable gels for retaining biocompatibility and/or compatibility with other components of the implant may be used. For example, the implant may comprise a silicone gel with high elasticity and/or low viscosity, e.g., a visco-elastic silicone material. In some examples, the implant may comprise a silicone gel with a penetration value ranging from 1.0 to 6.0, such as from 2.0 to 5.0, or from 5.0 to 6.0. The penetration value is a factor that measures the firmness of a colloid, such as a silicone gel. In some examples, the implant may comprise a silicone gel attaining a value in the range of 2 mm to 29 mm protrusion in the cone cohesion test and that will not detach from the cone, according to the test previewed in ISO 14607:2009 (Non-active surgical implants—Mammary implants—Particular requirements) and ASTM F703 (Standard Specification for Implantable Breast Prostheses).

Such materials may allow for more efficient compaction, elongation, and loading of the implant into an introducer device, such as those disclosed in U.S. Provisional Application No. 62/323,160, incorporated by reference herein. Moreover, such materials may facilitate insertion of the implants through a smaller incision in the patient, reducing common issues and risks associated with current surgical implantation methods, such as tearing of the shell, separation of the filling (gel) from the inner shell walls, or fracturing of the filling.

The implants and surfaces thereof disclosed herein may be produced using any suitable manufacturing process. For example, shells of implantable medical products according to some aspects of the present disclosure, such as, e.g., shell 102 shown in FIGS. 1A-1B, may be produced by dip-molding. Other exemplary methods of producing implant surfaces according to the present disclosure may include, for example, rotational molding, pour-molding, and casting.

Figure 8:
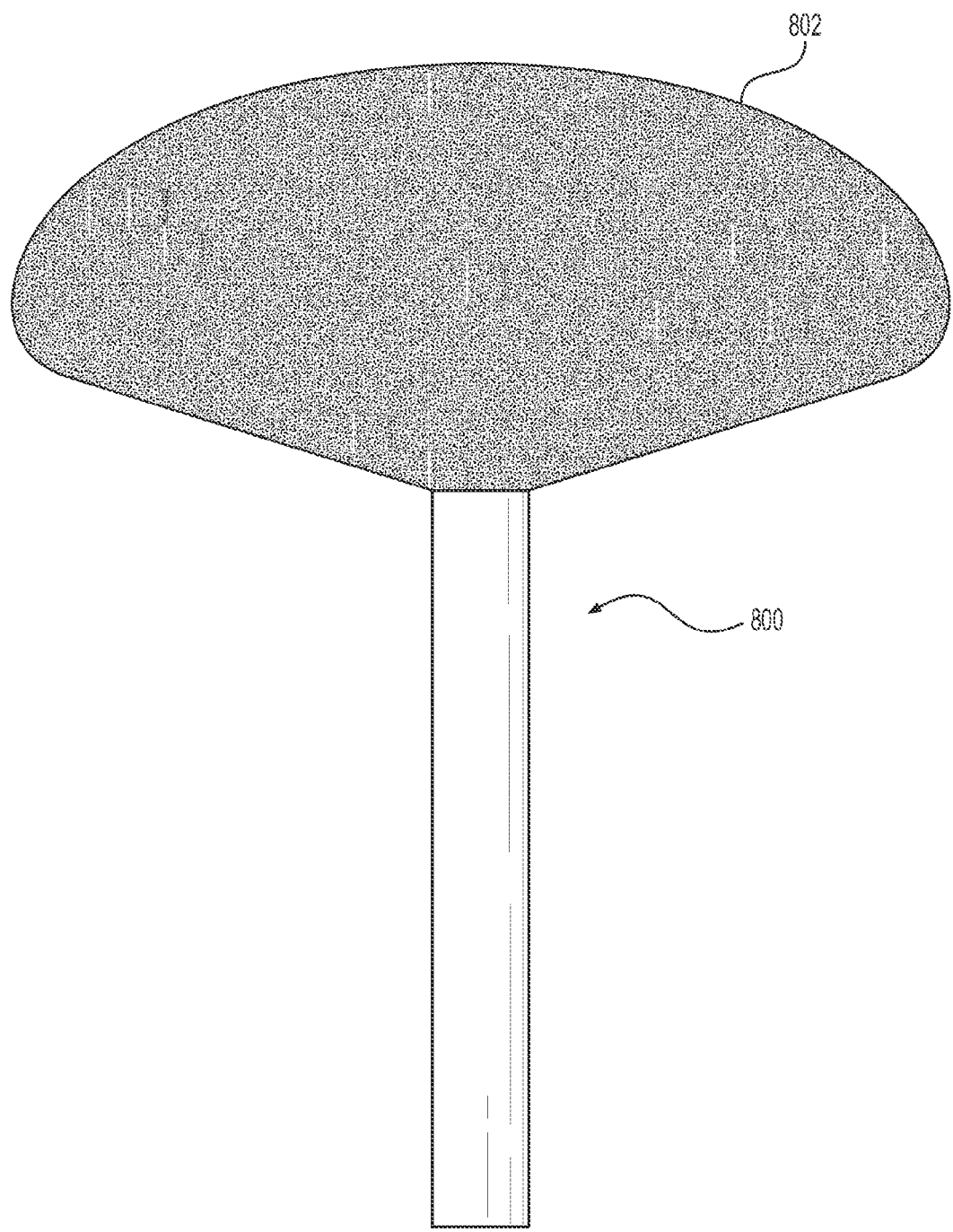
FIG. 8 shows an exemplary mandrel useful as an implant mold, according to some aspects of the present disclosure.

FIG. 8 depicts an exemplary mandrel 800 that may be used as a mold for an implant shell. The mandrel 800 may comprise a variety of materials, such as metals, metallic alloys, one or more polymers or copolymers, ceramic materials, wood, stone, coral, or any combination thereof. Exemplary metallic materials include, but are not limited to, aluminum and aluminum alloys. Exemplary polymer or co-polymer materials include, but are not limited to, polyoxymethylene (acetal copolymer), such as Delrin® acetal homopolymers produced by DuPont™. Any other polymer/copolymer materials suitable for providing a textured mold surface as discussed herein may be used.

In some embodiments, a mirror image of a desired surface texture may be imparted onto the upper surface 802 of the mandrel 800. Various techniques may be used to texturized the surface 802. For example, mandrel surface 802 may be impacted (e.g., blasted or sandblasted) with an abrasive substance, such as a plurality of abrasive particles. Exemplary materials for the abrasive particles may include, but are not limited to, staurolite minerals, quartz, kyanite, titanium minerals and/or their alloys, zircon, heavy metals (e.g., cadmium, selenium, ferrous iron, and/or steel alloys such as tungsten alloys, chromium alloys, magnesium alloys, molybdenum alloys, and vanadium alloys). These are exemplary materials, and other materials having comparable low malleability and high hardness as to maintain their shape characteristics during a blasting process may also be used for the abrasive particles. In some examples, the abrasive particles may be generally non-spherical in shape, e.g., irregular-shaped particles. For example, the particles may have a granular, irregular shape. In other examples, the abrasive particles may be generally spherical, ovoid, or otherwise regular in shape. In some examples, the abrasive particles may have generally rounded surfaces. In at least one example, the abrasive particles may comprise quartz, and may have generally rounded surfaces clean from extraneous debris, e.g., having less than about 7.0%, less than about 5.0%, less than about 3.0% free silica, or less than about 1.0% free silica.

The composition and shape of the particles may be selected based at least partially on the composition of the mandrel 800, e.g., to provide for a difference in Mohs hardness between the abrasive particles and the mandrel 800. In some examples, the abrasive particles may have a Mohs hardness ranging from 5.0 to 8.0, such as from 5.0 to 6.5, from 6.5 to 7.0, or from 7.0 to 8.0. For example, the abrasive particles may have a Mohs hardness that is 1-3 values greater than the material(s) of the mandrel 800. In at least one example, abrasive particles having a Mohs hardness of 6.5 to 7.0 may be used with poly oxymethylene (e.g., a black acetal copolymer, e.g., Delrin®) mandrel.

The average diameter of the abrasive particles may range from about 10 µm to about 500 µm, such as from about 50 µm to about 450 µm, from about 50 µm to about 250 µm, from about 50 µm to about 100 µm, or from about 75 µm to about 125 µm. In at least one example, the abrasive particles may comprise quartz with an average diameter ranging from about 50 µm to about 100 µm (e.g., a mesh screen size in the range of 50-100 µm). Thus, the blasting and sandblasting processes according to the present disclosure are distinct from shot blasting or shot peening, which is generally understood to use spherical metal particles >500 µm (e.g., shot particles on the order of several millimeters) to create spherical dents in the surface. Sandblasting, by contrast, produces a superior mold surface that results in medical implant surfaces of greater biocompatibility and having textures as discussed throughout this disclosure.

Abrasive particles may be blasted at the mandrel surface 802 from, for example, a nozzle. The distance between the nozzle and the mandrel surface 802 may also be adjusted to affect the surface texture. The distance between the nozzle and the mandrel surface may range from about 2 cm to about 75 cm, such as from about 5 cm to about 50 cm, from about 5 cm to about 25 cm, from about 25 cm to about 50 cm, from about 10 cm to about 35 cm, or from about 10 cm to about 25 cm.

In some embodiments, particles used to blast the mandrel surface 802 may be reused for subsequently blasting further mandrel surfaces. In such embodiments, the particles may be periodically replaced to ensure adequate consistency of particles used in multiple mandrel-blasting iterations. Following the treatment with abrasive particles, the mandrel surface 802 may include peaks and valleys that provide a mirror image of the desired surface texture for the implant.

In some aspects of the present disclosure, a shell may be prepared by dip-molding, using mandrel 800 as a mold, wherein the mandrel surface 802 has been texturized. For example, the mandrel surface 802 may be dipped, e.g., at least partially or fully submerged in a thermoplastic or thermosetting material, such as a silicone dispersion, such that the silicone material at least partially or fully coats the surface 802. The surface 802 may be repeatedly dipped in order to form a multilayered shell, such as shell 102 of FIGS. 1A-1B. In some examples, the surface 802 may be dipped at least twice, three times, or four times or more to form multiple layers. In some examples, the surface 802 may be dipped between five and six times. In other examples, the surface 802 may be dipped more than six times. The thickness of the shell may range from about 0.1 mm to about 1.2 mm, such as from about 0.2 mm to about 0.8 mm, from about 0.3 mm to about 1.1 mm, or from about 0.4 mm to about 0.6 mm. In some examples, the thickness of the shell may range from about 0.33 mm to 1.02 mm, e.g., a thickness of about 0.4 mm, about 0.5 mm, about 0.6 mm, about 0.7 mm, about 0.8 mm, about 0.9 mm, or about 1.0 mm.

As discussed above, each layer may have the same or different composition with respect to the other layer or layers. To prepare a shell comprising layers with different compositions, the mandrel surface 802 may be dipped in different materials, e.g., silicone dispersions having different viscosities and/or different types of additives. In some examples, the shell may include one or more barrier layers to inhibit or prevent the passage of liquid or gel materials through the shell. Exemplary materials suitable for the barrier layer(s) include, but are not limited to, diphenyl silicone elastomers, dimethyl silicone elastomers, diphenyldimethyl silicone elastomers, methylphenyl silicone elastomers, fluorinated silicone elastomers such as trifluoropropyl silicone elastomers, and combinations thereof. Such barrier layers may be colored, e.g., by adding one or more pigments to the material(s) forming the barrier layer(s), to facilitate examination of the continuity and/or integrity of the barrier layer(s). For example, the barrier layer(s) may comprise a metal-based, inorganic, and/or organic pigment to provide a barrier layer that is blue, green, yellow, red, orange, purple, or any combination or hue thereof. For example, the barrier layer(s) may comprise a pigment such as phthalocyanine blue (e.g., copper chlorophthalocyanine) to provide a blue color. In at least one example, the shell may comprise one or more barrier layers comprising a two-part silicone elastomer comprising a diphenyldimethyl polysiloxane polymer dispersed in xylene and copper chlorophthalocyanine pigment dispersed in a vinyl-functionalized silicone polymer. Any of the materials and/or features of a barrier layer disclosed in U.S. Application Publication No. 2015/0150675, incorporated by reference herein, may be used in the present disclosure.

Once the appropriate number of layers have formed around the mandrel 800, the material(s) may then be allowed to cure at an appropriate temperature. For example, the shell may be cured at a temperature ranging from about 100° C. to about 200° C., such as from about 125° C. to about 175° C., or from about 125° C. to about 150° C. In some examples, the curing temperature may range from about 125° C. to about 127° C., e.g., about 125° C., about 126° C., or about 127° C. In further examples, the curing temperature may be about 150° C. The cured shell may then be removed from the mandrel 800 and inverted or turned inside out. Thus, the surface of the shell formerly in contact with surface 802 of mandrel 800 forms the exterior surface of the shell having a texture that is a mirror image of the textured surface 802 of the mandrel 800. Alternatively, the cured shell may be removed from the mandrel 800 and may not be turned inside out, resulting in a shell having a textured interior surface. Advantageously, imparting a mandrel or other mold with a texture that is the mirror image of a desired surface texture as described herein, and using the mandrel or other mold to create an implant with that surface texture, may allow for superior control over the characteristics of the implant surface as compared to other methods of texturizing a surface, such as rubbing an abrasive material across the surface. Additionally, the methods herein may allow for reproducibility in implant characteristics, and consistent production of multiple textured implant shells having the desired surface characteristics (e.g., roughness, kurtosis, skewness, peak heights, valley depths, peak density/distribution, contact angle, etc.).

According to some aspects of the present disclosure, textured mold surfaces may be produced by rotational molding (also called rotomolding) processes. For example, the interior surface of a rotational mold may be impacted with an abrasive substance, such as a plurality of abrasive particles in a manner similar to the preparation of mandrel surface 802 described above. Thus, when thermoplastic or thermosetting material(s) (such as, e.g., silicone material(s)) are placed into the hollow textured rotational molding cavity—and the mold is rotated around—the material(s) may spread evenly over the interior surface. Once the material(s) are cured and the shell component is removed from the rotational mold, the surface of the shell component formerly in contact with the interior surface of the rotational mold may have a texture that is a mirror image of the textured surface of the interior surface of the mold. The textured surface of the shell may define the outer surface, such that the shell need not be inverted.

In another exemplary process suitable for preparing the surface textures herein, a masking mold may be used. Molding masks may be useful, for example, in preparing integral surfaces having areas or regions with different surface characteristics, including the types of surfaces illustrated in FIGS. 7A-7G. For example, a masking mold whose surface includes peaks and valleys having a desired micro-texture may be used in a controlled imprinting process to create an implant surface with select areas having greater or less roughness than other portions of the surface. Exemplary materials for the masking mold may include, but are not limited to, one or more metals, a metallic alloys, etchable polymers, etchable co-polymers, or a combination thereof. In at least one example, the masking mold may comprise an aluminum alloy.

In some exemplary processes, a mandrel surface may be engraved with a label or other identifying marks (e.g., label 706 depicted in FIGS. 7A-7G), before or after being blasted with particles or subjected to a masking mold. For example, a mandrel surface 802 may be engraved with a label prior to being blasted with particles, and the engraved portion of the surface may be protected by a masking material during the blasting process to preserve the label. In further exemplary processes, a masking mold may be used to imprint a mandrel surface with a label or other identifying marks, either before or after the application of other texturizing processes to the mandrel surface.

The surface of the masking mold may be texturized by any of the methods disclosed herein, such as impacting the surface with abrasive particles to yield the desired roughness and/or other surface characteristics or parameters. The masking mold then may be constructed or cut into the size and shape of the area to have those surface characteristics. For example, the masking mold may be cut or constructed into one or more shapes as depicted on the implant surfaces pictured in FIGS. 7A-7G. The masking mold shapes may then be affixed to the surface of an implant mold, e.g., surface 802 of mandrel 800, by an adhesive or other suitable material or mechanism. The implant mold and masking mold affixed thereto then may be subjected to a controlled electro-chemical deposition process to etch (imprint) the micro-texture characteristics of the masking mold into the surface of the implant mold. After this treatment of the implant mold, an abrasive blasting process as discussed above may be performed to texturize other portions of the mold. Additionally or alternatively, an abrasive blasting process may be used to texturize the implant mold prior to imprinting specific areas of the implant mold with a specified surface texture, e.g., via an electro-chemical deposition process.

Using a texturized mold in an implant manufacturing process may provide for a more consistent and uniform texture on any or all surfaces of the implant (e.g., top, sides, and base) as compared to prior methods of applying abrasive materials directly to the implant surface, and may yield less propensity towards embedding abrasive particles in the implant shell material. For example, the process described above for preparing a texturized mold surface may result in few to no residual abrasive particles detectable on the mold surface after the surface treatment, which in turn may result in few to no loose particles in or on a shell made using the mold. Further, the preparation of mold surfaces (e.g., texturizing the surface of a mandrel) may allow for control over the surface texture of an implant, such that desired surface texture properties (e.g., roughness, kurtosis, skewness, peak heights, valley depths, peak distributions, etc.) may be selected and imparted to the surface of the mold as desired. The preparation of texturized mold surfaces may also provide for uniformity in manufacturing implants with the same or similar surface characteristics, e.g., having surface characteristics of the desired value or falling within the desired range of values. Thus, for example, the methods herein may allow for molds having a set of fixed, consistent surface features on a desired scale (e.g., nanometers or micrometers) for manufacturing a shell having a surface with a hierarchical (i.e., controlled), nano- and/or micro-structured texture.

As mentioned above, interior surfaces of an implant may be prepared with a surface texture. In some embodiments, for example, it may be desirable to impart texture to the interior of an implant shell, such as surface 106 of shell 102 of FIGS. 1A-1B. In some examples, the shell may be prepared such that both the interior and exterior surfaces, e.g., surfaces 104, 106 of shell 102, may have a surface texture as disclosed herein. For example, a roughened texture may help to maintain contact between the filling material and the shell, e.g., to reduce or eliminate potential separation between the implant shell and filling material, such as a gel filling, inside the shell.

Texture may be imparted to the inner surface of a shell by abrading a not-yet-cured material layer that is to define the innermost surface of an implant shell. For example, in a shell created by a dip-molding process using a mandrel such as mandrel 800, several layers of a shell material dispersion, such as a silicone elastomer dispersion, may be coated over the mold as discussed above. Texture may be applied to the outermost layer formed by the last dip. Before curing the shell, for example, particles comprising salt or other abrasive material may be sprayed, bombarded, or otherwise applied to the uncured final-dipped layer of the shell on the mold such that the salt sticks to the surface. The shell having the salt particles may be cured, and then the salt dissolved and washed away, or otherwise removed, to leave a rough or roughened surface. Upon removal of the particles from the shell, the shell may be removed from the mold and inverted such that the roughened surface created by the salts will be located on the interior of the shell. When the surface of the implant mold is texturized, both the inner and outer surfaces of the shell may have texture, e.g., wherein the surface characteristics of the inner and outer surfaces may be similar in some respects, or may be different. In some examples, the outer surface may be a hierarchical, nanostructured surface, and the inner surface may be a less controlled, rougher surface. That is, the texture of the outer surface may be more controlled and well-defined than the inner surface.

In another exemplary embodiment, a texturized inner surface of a shell may be created by adjusting the solvent content of the solution used for the final-dipped layer of the shell and/or by increasing the cycle temperature used for curing. Alternately or additionally, the pressure (e.g., in a curing oven) used for curing the shell may be decreased. One or more of these changes may cause solvent in the final-dipped layer of the shell to boil as it cures, creating pits and craters that may increase the total surface area in this final-dipped layer of the shell. Upon removal of the cured shell from the mold and inversion of the shell, the pitted and cratered surface may define the interior surface (e.g., interior surface 106 of shell 102 in FIGS. 1A-1B).

In some examples, a combination of the above-described methods of texturizing the inner and outer surfaces of an implant shell may be used. For example, a biocompatible texture according to the present disclosure may be imparted on the outside of an implant shell with a texturized mandrel. For example, prior to dipping or otherwise coating the mandrel with a silicone dispersion (or other suitable thermoplastic or thermosetting material) to create the implant shell, the mandrel may be blasted with abrasive particles, e.g., uniformly-sized abrasive particles. Once the mandrel has been thus treated, layers of the shell material may be applied to the mandrel to build the shell. Then, the above-described texturizing processes may be applied to the final-dipped layer of the shell. The shell then may be removed from the mandrel and inverted, such that the outer surface has a biocompatible surface texture with specified roughness, kurtosis, and/or skewness values, and the inner surface also has texture. In some embodiments of the present disclosure, the inner surface texture may be markedly rougher and less consistent or controlled than the texture of the outer surface.

As has been described above, some implants according to the present disclosure may include a shell, e.g., enclosing a filling material. Such implant shells, e.g., implant shell 102 shown in FIGS. 1A-1B, may have an aperture or hole, which may be created during the implant shell molding process. A patch, such as patch 112, may be affixed to the implant shell over the hole, to cover and "stopper" the hole. In further embodiments, a patch may be applied to a portion of a shell or other portion of an implant surface where there is no hole, e.g., to provide a different texture to that portion of the implant surface. Such patches may be texturized, for example, by preparing both a shell having an aperture, and a patch for covering the aperture, with surface textures in accordance with the present disclosure. By affixing the patch over the aperture of the shell, the entire exterior implant surface may have texture as disclosed herein. In some examples, the patch may be prepared with a higher roughness than the rest of the shell, which may help to provide increased friction between the surface of the implant and surrounding tissues, e.g., and thus decreased movement of the implant as a whole.

To create a patch having a desired surface texture according to the present disclosure, a patch (e.g., patch 112 of FIGS. 1A and 1B) may be prepared with an unvulcanized surface, and may be positioned into a hole of an implant shell, such as shell 102, in which filling 114 may have been introduced. A vulcanizing foot of a heat vulcanizer may be blasted with an abrasive substance, such as the abrasive substances disclosed herein. The vulcanizer may then be used to compress the patch to the shell over the hole in the shell. During vulcanization, the textured, hot, vulcanizing foot may imprint the patch with the texture on the vulcanizer foot while the patch-to-shell connection is heat-cured. Upon removal from the vulcanizer, the patch area of the shell may have the desired texture surface.

In another exemplary process, a flat sheet of patch material may be texturized using an imprinting mold that has been impacted with abrasive particles, as described above. Patches then may be punched or cut out of the sheet and applied to the shell using a suitable material, such as adhesives or "raw" (e.g., unvulcanized) sheeting material that may be placed in between a patch and a shell, and vulcanized to attach the patch to the shell, or by a suitable process such as a welding process using, e.g., ultraviolet (UV), infrared (IR), or other laser-generated light energy.

As mentioned above, it is believed that the surface textures disclosed herein may contribute to the biocompatibility of medical implants including such textures. In some aspects, for example, implants with the surface characteristics disclosed herein may be associated with reduced inflammation of the surrounding tissue. Medical implants with surfaces prepared as described herein may increase implant biocompatibility, and/or may reduce or eliminate micro-ruptures of the implant, which may present safety risks to the patient and reduce the longevity of the implant. Without intending to be limited by theory, it is believed that medical implants having the surface characteristics discloses herein may help to reduce or eliminate adverse physiological response by the tissue surrounding the implant, such as double capsular contracture. For example, implants having surface textures as disclosed herein may provide for capsular contracture rates associated with secondary surgeries that are lower than 1.0%. Further, for example, implants with surface textures as disclosed herein may be implicated or associated with fewer implant ruptures, e.g., providing for a rupture rate lower than 1.0%. For example, the processes discussed above used to prepare the surface textures may minimize the creation of micro-fractures on the implant surface, which may help to reduce the incidence of rupture.

The implants herein may include various features to assist in maintaining the location, position, and/or orientation of the implant over time. For example, in addition to, or in lieu of, the implant being formed with an integral surface texture, implants according to the present disclosure may include one or more tabs attached or otherwise coupled to a surface of the implant to assist in implant fixation. Each tab may have a surface texture with surface characteristics (e.g., roughness, skewness, kurtosis, peak height, valley depth, and/or contact point density) that is the same or different than the surface characteristics of another portion of the implant surface. Such tabs include, but are not limited to, reinforced tabs, such as silicone-reinforced tabs. For example, the outer surface 104 of implant 100 may include one or more silicone-reinforced tabs attached to the posterior side 110 of the implant 100 in a specified configuration or pattern. Exemplary configurations or patterns include those illustrated in FIGS. 7A-7G, wherein the various areas 708, 710, 712, 714, may be defined by tabs as discussed above.

Each tab may be positioned in a specific pre-determined location and orientation, e.g., for device fixation to restrict or prevent rotation or other movement of the device. Such tabs may be constructed as separate pieces of material that are attached to the larger body of the implant. In some aspects, the tabs may be configured to protrude outward from the surface of the implant, e.g., to increase the surface area of the implant in contact with the patient tissue. In further aspects, the tabs may be configured to rest flat against or flush with the surface of the implant. Such tabs may be attached to the body of the implant via, for example, a suitable adhesive or combination of adhesives, by welding techniques, and/or by fusion processes, which may be designed not to jeopardize the integrity of the implant (e.g., the integrity of an elastic shell) upon attachment of the tab(s). Such tabs may be formed with texturized surfaces, such as the texturized surfaces of the present disclosure.

According to some aspects of the present disclosure, the implant may comprise one or more support elements in addition to, or as an alternative to, a texturized surface. Such support elements may extend outward from the implant for attachment to an anatomical feature of the patient to assist in implant fixation. In some embodiments, the support element may comprise a flexible strap and/or a fixation device. For example, one or more straps may extend from the implant surface to anchor the implant to a portion of the patient's anatomy. Such strap or straps may having a first end extending from the implant and a second end configured for attachment to an anatomical feature or structure of the patient. In some aspects, each strap may comprise a thin piece of elastic material, forming a suspension strap of a relatively thin diameter. Exemplary materials suitable for the strap(s) include, but are not limited to, biocompatible polymers, such as biocompatible reinforced polymer elastomeric materials compatible or integral with the shell material. The strap(s) may have a generally circular cross-section or may be substantially flat. In some aspects, the strap(s) may comprise a reinforced material, e.g., to provide the straps with rigidity to assist in anchoring.

Referring to a breast implant, for example, the strap(s) may be attached to the upper posterior and/or anterior portion of the implant shell, e.g., the strap being molded or adhered directly into the shell, or formed as an integral extension of the shell. The strap(s) may be configured to attach to the clavicle or other internal structure of the patient, e.g., for fixation to bone. Upon implantation, for example, the strap(s) may extend upward through a relatively narrow subcutaneous tunnel to connect the implant to the clavicle.

Figure 9:
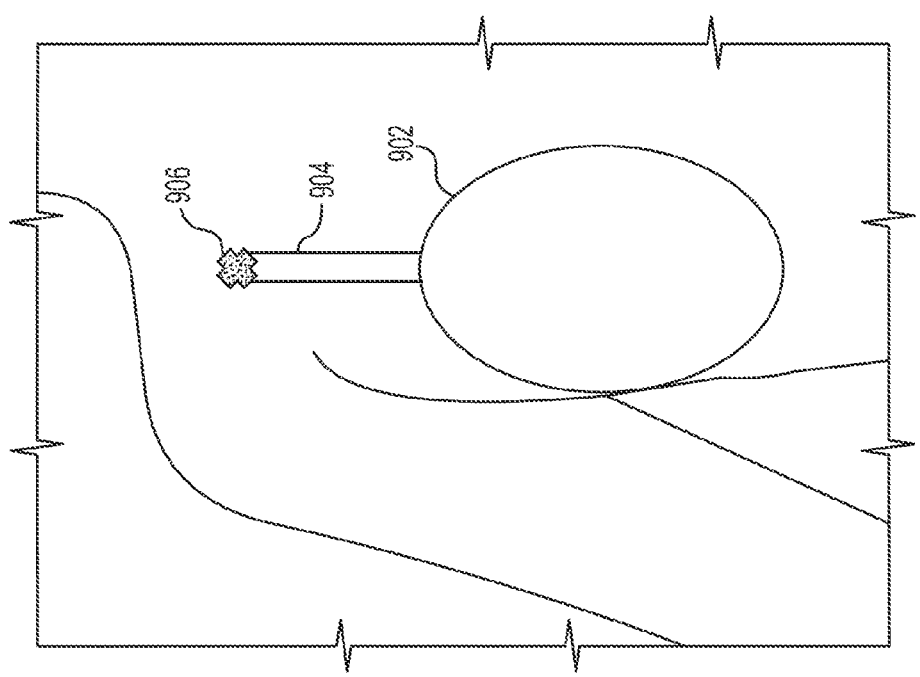
FIG. 9 illustrates an exemplary support element, according to some aspects of the present disclosure.

FIG. 9 illustrates, in schematic form, the positioning of an exemplary breast implant 902 having a support element in the form of a strap 904 and a fixation device 906. The fixation device 906 may comprise any suitable fixation structure, such as one or more of a bone screw, suture, and/or staples, among other fixation devices and related mechanisms. Strap 904 may be elastically biased or deformable (e.g., similar to a rubber band) in the longitudinal direction, or may otherwise be flexible to allow some limited movement of the implant 902 while ensuring that the implant returns to its original position. In at least one example, strap 904 may be texturized, e.g., having surface characteristics with specific roughness, kurtosis, and/or skewness values as disclosed herein.

Figure 10A:
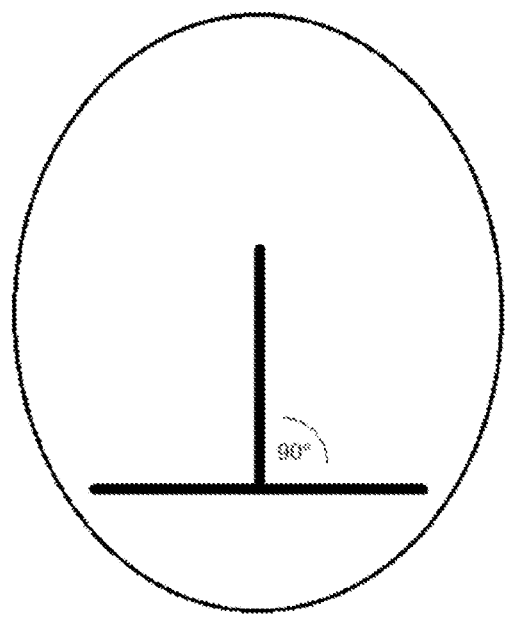
FIGS. 10A and 10B show exemplary positioning/orientation markers of an implant, according to some aspects of the present disclosure.
Figure 10B:
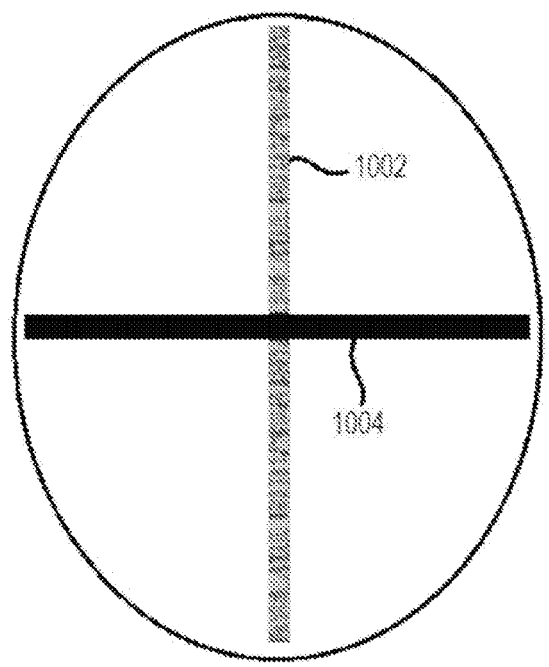

Implants according to the present disclosure may include one or more features visible by imaging, e.g., to assist in monitoring the location, position, and/or orientation of the implant over time. For example, the implants may include one or more radiopaque markers. In some examples, the radiopaque markers may be in the shape of strips as illustrated in FIGS. 10A and 10B, or any other suitable shape. Each strip may have a particular orientation, e.g., in specific horizontal and/or vertical directions, to allow physicians to more easily determine movement, orientation, and/or position of the implant during and/or after implantation. FIG. 10A depicts, in schematic form, a configuration of radiopaque strips 1001 in an implant, such as a breast implant. In some embodiments, the implant may include a plurality of radiopaque markers, which may comprise the same or different materials. FIG. 10B depicts, for example, a configuration of a vertical orientation radiopaque marker 1002 in an implant, and a horizontal orientation marker 1004 in the implant. The radiopaque markers 1002, 1004 may comprise different materials, providing for two different radiopaque densities. Thus, for example, the markers 1002, 1004 may be distinguishable from each other, e.g., to allow for measuring device rotation post-implantation.

Additionally, or alternatively, implants according to the present disclosure may include one or more radiopaque salts or other radiopaque particulate materials to assist in monitoring location, position, and/or orientation of the implant. For example, radiopaque salts may added to a liquid or gel filling material before or after the filling material is introduced into the implant. Examples of radiopaque materials suitable for a filling material include, but are not limited to, barium sulfate, bismuth compounds, tungsten, tantalum, and platinum, among other radiopaque metals or metal alloys. In some aspects, the implants herein may comprise powered radiopaque materials.

The implants herein may comprise from about 10% to about 45% of particulate radiopaque materials, by weight with respect to the weight of the implant, such as from about 15% to about 30% by weight, or from about 20% to about 25% by weight. In at least one example, the implant comprises a shell comprising a filling material such as a saline solution or a silicone gel and a radiopaque salt or a combination of radiopaque salts. For example, the amount of the radiopaque materials incorporated into the filling material may be selected so as to avoid altering and in order to not jeopardize the viscosity characteristics of the filling material. Such radiopaque features may not only allow the physician to assess movement, misalignment, and/or rotation of the implant, but also may indicate a breach in the shell allowing the filling material to seep through the shell into the surrounding tissue. For example, radiopaque materials escaping through a breached shell may give the appearance of a bleb or irregular extension of the surface of the implant in a radiograph. A physician may image a patient during a procedure and/or after a procedure (including during periodic check-ups) to verify the integrity of the implant over time.

Implants according to the present disclosure may be, for example, single-use sterile implants. In some embodiments, implants according to the present disclosure may include a unique device identifier (UDI), such as a micro-transponder, for post-implantation device recognition and traceability. Any of the devices and features disclosed in U.S. Provisional Application No. 62/313,218, filed on Mar. 25, 2016, and/or U.S. Application Publication Nos. 2014/0081398 and/or 2014/0078013, each incorporated by reference herein, may be used in the present disclosure.

As mentioned above, in some embodiments, the implant may comprise a shell configured to prevent or delay passage of a filling material through the shell to contact tissue. For example, the shell may comprise two or more different low viscosity, heat-curable silicone dispersions, wherein one of the silicone dispersions may form a barrier layer. Thus, for example, a first silicone dispersion may form a base of the layers of the shell, and a second silicone dispersion may comprise a barrier layer to prevent or delay the passage of filler through the shell to reach patient tissue. Optionally, additional silicone dispersions may form additional layers of the shell above or below the barrier layer.

Implants according to the present disclosure may have a variety of different shapes, sizes, and/or volumes, depending on patient preference, anatomy, and/or need. In some aspects of the present disclosure, different parameters may be selected to produce a customized implant, such as a breast implant for breast augmentation and/or reconstruction surgery. Such parameters may include, for example, a surface texture having a set of pre-determined characteristics (e.g., roughness, kurtosis, skewness, peak height, valley depth, contact point density), and combinations of surface textures and characteristics as disclosed herein, as well as other implant parameters such as shape, volume, type of filling material, and viscosity of the filling material. Any features regarding customizing implants discussed in U.S. Provisional Application No. 62/318,402, incorporated by reference herein, may be used in the present disclosure.

FIG. 11 depicts some exemplary shape and positioning parameters of implants which can be adjusted to create a custom-sized and custom-shaped implant. For example, an overall implant shape, such as a teardrop shape 1102 or an oval shape 1104, may be selected. When viewed from an anterior or posterior viewpoint, the widest width of an implant having a teardrop shape 1102 may be located lower than a horizontal center line of the implant. In contrast, the widest width of an implant having an oval shape 1104 may be located at or substantially near the center line of the implant.

An overall implant height 1106 and/or width 1108 may also be selected from, for example, a range of heights and/or widths designed to suit a variety of patients. A projection distance 1110, representing the distance from the most anterior portion of the implant to the posterior portion (the portion to be placed closest to the patient's chest cavity), may also be customized. An apex position 1112 may also be selected to customize an implant. Apex position 1112 may represent, for example, a vertical positioning of the most anterior portion of the implant relative to the lowest portion of the implant. FIG. 11 depicts, for example, four different height options for apex position 1112. Further, an upper pole location may also be customized for an implant. For example, selection of upper pole location 1114 would result in an implant having a more convex or linear shape from the top of the implant to the apex, or the most anterior portion of the implant when the implant is placed in a patient. Selection of upper pole location 1116, in contrast, may provide for an implant having a more concave shape from the top of the implant to the apex.

Such size and/or positioning parameters may be selected in combination with surface texture. For example, any combination of size and/or positioning parameters may be selected in combination with one or more surface textures prepared according to the present disclosure for the outer surface of an implant. In some examples, surface textures for both outer and inner surfaces of an implant shell may be selected in combination with size and/or positioning parameters. For example, a relatively rough-textured inner surface or an untextured inner surface may be selected in combination with an outer surface having a hierarchical nanostructure (e.g., controlled characteristics of roughness, kurtosis, and/or skewness as discussed above), and further in combination with one or more size and/or positioning parameters. In further examples, one of a variety of configurations of an outer surface texture (such as those depicted in, e.g., FIGS. 7A-7G and others described herein) may also be selectable in combination with other selectable parameters. In further examples, a customized label (e.g., label 706 in FIGS. 7A-7G) may also be selected in combination with outer surface textures, an inner surface texture, and/or other parameters.

In some embodiments, one or more shell and/or filling materials may also be selected in combination with other implant parameters. For example, a shell having one or more colored or transparent barrier layers to inhibit or prevent the passage of liquid or gel through the shell may be selected in addition to other parameters. In further examples, a desired gel or other filling material may also be selected. In yet more embodiments, additional features may also be selected in combination with desired size, shape, positioning, surface texture, and other parameters. For example, one or more tabs and/or straps to aid in fixation may be selected, as well as sizes and positions of such tabs and/or straps. In further examples, one or more radiopaque materials may also be selected for addition to an implant, such as radiopaque salts to be added to the gel or filling material, and/or radiopaque markers.

In some embodiments of the present disclosure, customized implant parameters, such those disclosed herein, may be selected prior to manufacturing an implant mold or mandrel, such as mandrel 800. In some embodiments, mandrel 800 or another mold used to manufacture a customized implant as disclosed herein may be manufactured to be a particular size and/or shape using customized parameters selected by a particular patient, practitioner, or manufacturer. In some embodiments, a customized mandrel or mold may be, for example, three-dimensionally printed. In some embodiments, after initial manufacture or printing of a customized mold or mandrel, one or more surfaces of the mold or mandrel may be treated as disclosed herein (e.g., blasted with abrasive particles) in order to impart one or more desired surface textures to an implant of a desired custom shape and/or size, to be manufactured using the customized mold or mandrel.

The following examples are intended to illustrate the present disclosure without, however, being limiting in nature. It is understood that the present disclosure encompasses additional embodiments consistent with the foregoing description and following examples.

EXAMPLES

Example 1

A breast implant is prepared as follows. The shell of the breast implant is prepared with a mandrel comprising Delrin® textured with a staurolite sand and mineral mix of particles having a diameter ranging from 50-420 μm, and a Mohs hardness ranging from 6.5-7. The texturized mandrel is dipped a total of five to six times into a dispersion of a siloxane polymer elastomer, until a coating having a total thickness of about 1.0 mm is achieved to form the uncured shell. The dipped mandrel is then cured at a temperature of 126° C. The cured shell is then removed from the mandrel and inverted, such that the surface formerly in contact with the texturized mandrel surface is the outermost surface of the shell. The shell then is filled with a silicone gel. Air is removed from the shell, the shell is sealed, and the silicone gel is cured.

Surface properties including the average roughness, the skewness value, and the kurtosis value of the shell are measured using a confocal laser microscope or an optical profilometer. The shell measures an average roughness ($S_a$) of 3.1 µm, a skewness value of 0.89, and a kurtosis value of 4.76 (normalized kurtosis value of 1.76). A 3D non-contact microscope is used to measure the density of contact points of the shell surface. The shell surface has a density of contact points ranging from 40,000 peaks/cm² to 50,000 peaks/cm².

Example 2

Figure 5:
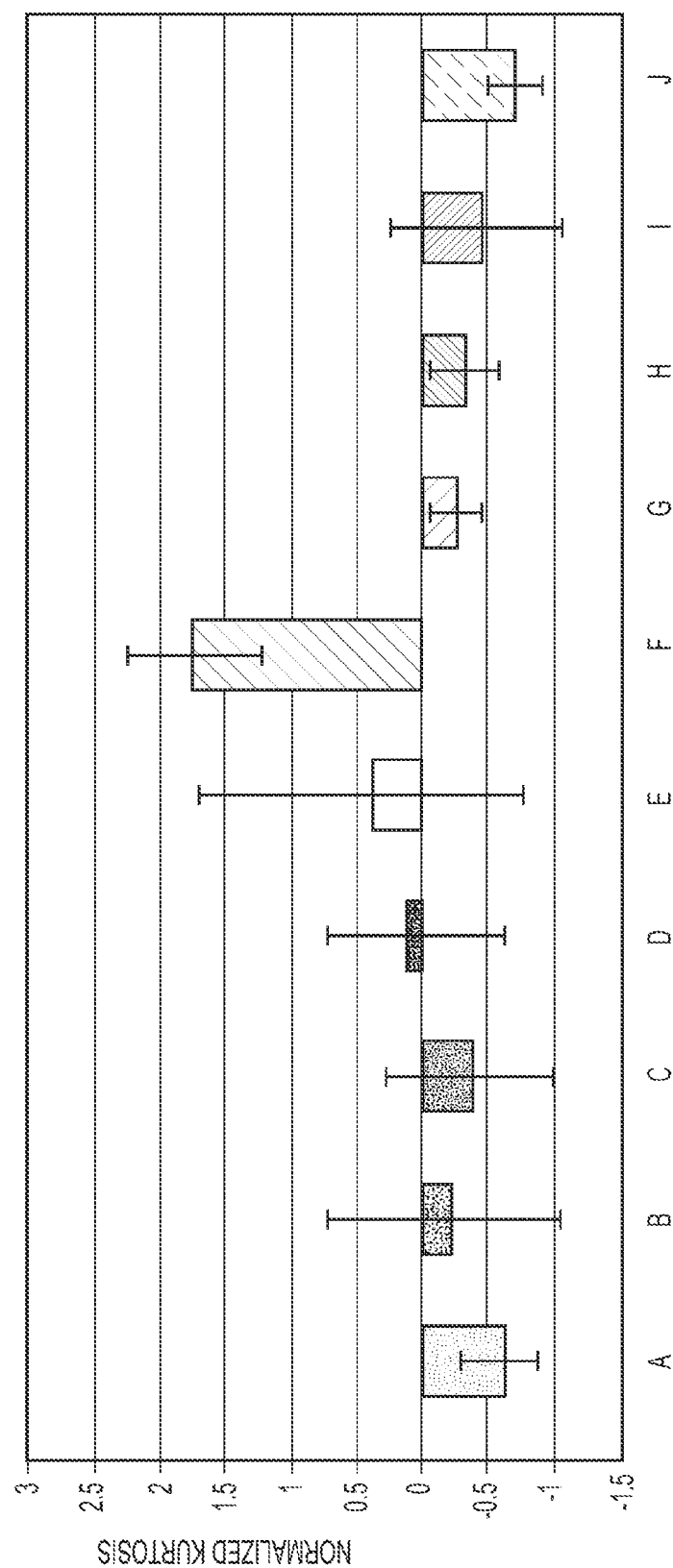
FIG. 5 is a graph comparing the kurtosis values of various breast implants, as discussed in Example 2.

Normalized kurtosis values were measured for the surfaces of several commercial breast implants (surfaces A-J), as summarized in Table 2. A Keyence confocal laser microscope (Keyence Corporation, USA) was used to measure surface roughness for each implant to determine the normalized kurtosis value. Measurements were processed using the Gwyddion program for modular scanning probe microscopy data visualization and analysis. Results are summarized in Table 2.1 below and shown in FIG. 5.

TABLE 2.1

| Surface | Product | Normalized kurtosis value |
|---|---|---|
| A | Biocell ® (Allergan) | −0.6 |
| B | Polytech | −0.2 |
| C | Sebbin | −0.4 |
| D | Cereform ® (Cereform Ltd.) | 0.1 |
| E | Silimed | 0.45 |
| F | SilkSurface ™-Gen 1 (Motiva) | 1.75 |
| G | Siltex ® (Mentor) | −0.25 |
| H | VelvetSurface ™ (Motiva) | −0.35 |
| I | Eurosilicone (GC Aesthetics) | −0.45 |
| J | Mentor Smooth | −0.70 |

Surface characteristics for SilkSurface™—Gen1 and VelvetSurface™ breast implants (Motiva, Establishment Labs) were measured and compared to the surface characteristics of breast implants prepared as described in Example 1. Results are shown in Table 2.2. Measurements were performed with a Dektak-XT stylus profiler, and surface characteristics were calculated according to standard ISO 4287: 1997.

is believed that a mean surface profile (the average of peak heights and valley depths across the surface profile) near the maximum peak height and maximum valley depth, combined with a kurtosis value above Gaussian distribution (indicating more uniformity in peak heights and valley depths), a positive, near-zero skewness value (indicating symmetry of peaks and valleys), and a high contact point density, provides for lower adverse physiological reactions, a reduction in immune response, and less capsular contracture. For example, Table 2.2 shows that the surface according to the present disclosure exhibited a greater peak height and greater total surface profile height as compared to the SilkSurface™—Gen1 breast implant. Implant surfaces according to the present disclosure are expected to provide greater biocompatibility, e.g., for fibroblast cell alignment.

Example 3

Several silicone materials prepared according to the procedure of Example 1 were tested for hydrophobicity as an indicator of biocompatibility. A set of ten silicone shells having an average roughness value $R_a$ of ~4 µm was prepared as described in Example 1. A scalpel was used to cut three rectangular pieces out of each shell, at the base (located on the posterior side of the shell as it would be implanted in a patient), the equator (located around the portion of the shell having the largest diameter), and the apex (located at the anterior-most point of the shell as it would be implanted in a patient). A total of 30 samples mounted onto slides were thus prepared. Pieces cut from the base and apex measured approximately 1 cm×2 cm in area, and pieces cut from the equator measured approximately 1 cm×3 cm. Samples from the equator of each shell were cut such that the long edge of each sample was oriented in the direction from the base of the shell to the apex. Each sample was loaded onto a microscope slide in substantially the same orientation as other samples from the same implant location.

Contact angle measurements were performed at room temperature (20° C.) and ambient humidity (85%) using a ramé-hart goniometer CAM 200 system (ramé-hart instrument co., USA). For each measurement, a single drop of water having a volume between 0.5-1.0 µl was placed on the surface of the sample manually with a micropipette. Contact angle measurements were taken at t=0 and at t=10 minutes.

TABLE 2.2

| Surface characteristic | SilkSurface ™-Gen1 | VelvetSurface ™ | Present disclosure |
|---|---|---|---|
| Average roughness ($S_a$) | 3.5 µm ± 0.1 µm | 17.0 µm ± 3.0 µm | 4.0 µm ± 1.0 µm |
| Skewness ($S_{sk}$) | 0.6 | 0.1 ± 0.2 | 0.4 ± 0.2 |
| Kurtosis ($S_{ku}$) | 2.7 | 2.6 ± 0.3 | 3.1 ± 0.4 |
| Maximum peak height | 7.9 µm ± 0.4 µm | 43.0 µm ± 9.0 µm | 14.0 µm ± 2.0 µm |
| Maximum valley depth | — | 41.0 µm ± 6.0 µm | 12.0 µm ± 2.0 µm |
| Total Height of Surface Profile (max. peak height + valley depth) | 15.0 µm ± 1.0 µm | 85.0 µm ± 12.0 µm | 25.0 µm ± 4.0 µm |
| Mean Height of Surface Profile (avg. peak height + valley depth) | — | 57.0 µm ± 15.0 µm | 13.0 µm ± 2.0 µm |
| Contact point density (peaks/cm²) | — | — | 40,000-50,000 |

Without being bound by theory, it is believed that the combination of surface characteristics listed above for the surface according to the present disclosure exhibits superior biocompatibility properties, as compared to the other breast implants listed in Tables 2.1 and 2.2 above. For example, it This was repeated for three separate drops of water on the surface of each sample to avoid local effects caused by irregularities in a particular spot.

Table 3 lists the average contact angles obtained for the samples, where "avg. initial CA" refers to the average contact angle measured at t=0, "avg. final CA" refers to the average contact angle measured at t=10 minutes, and "avg. CA" refers to the average of the measurements at t=0 and t=10 minutes.

TABLE 3

| Sample location | Avg. Initial CA (°) | Avg. Final CA (°) | Avg. CA (°) |
|---|---|---|---|
| Equator | 131 ± 3 | 107 ± 8 | 119 |
| Apex | 132.6 ± 3 | 108.7 ± 8 | 121 |
| Base | 129.2 ± 5 | 105 ± 7 | 117 |
| Combined* | 131 ± 2 | 107 ± 4 | 119 ± 2 |

*Average contact angles of equator, apex, and base combined

As shown by the difference between initial contact angle measurements and final contact angle measurements, the water droplets initially retained more of their shape (exhibited a higher contact angle with the surface), and then spread somewhat across the surfaces over time, by t=10 minutes. This was understood to relate to the types of forces between the water droplet and surface, e.g., an initial interaction driven primarily by physical forces (e.g., roughness, pore size, etc.) that are overshadowed by chemical forces (e.g., determined by the chemical properties of the implant material). Both the initial and final contact angle measurements demonstrate that the samples exhibit overall hydrophobicity, with higher initial hydrophobicity. Such hydrophobicity of the surface may provide for improved biocompatibility between implant surfaces and patient tissue.

Any aspect or feature in any embodiment may be used with any other embodiment set forth herein. It will be apparent to those skilled in the art that various modifications and variations can be made in the disclosed implants, implant features, and processes without departing from the scope of the disclosure. Other embodiments will be apparent to those skilled in the art from consideration of the specification and practice of the disclosure disclosed herein. It is intended that the specification and examples be considered as exemplary only.

What is claimed is:

1. A method of manufacturing, the method comprising:
applying a biocompatible material to a mold surface of a mold to form a shell of a medical implant, wherein the mold surface is prepared by sandblasting the mold surface with a plurality of abrasive particles, wherein an implant surface of the implant in contact with the mold surface and has an even distribution of peaks having a height of 15 μm±5 μm and an even distribution of valleys having a depth of 15 μm±5 μm;
removing the shell from the mold;
inverting the shell so that the implant surface is an outermost surface of the implant; and
filling the shell with a silicone gel so that the silicone gel covers an inner surface of the shell;
wherein the medical implant is configured for uniform radial compression, such that the medical implant withstands elongation and compacting forces during minimally-invasive surgery without separation of the silicone gel from an inner surface of the shell.

2. The method of claim 1, wherein the implant surface has a kurtosis value ranging from 2.5 to 3.5.

3. The method of claim 1, wherein the implant surface has a kurtosis value ranging from 3.5 to 5.

4. The method of claim 1, wherein the implant surface has a kurtosis value ranging from 4 to 7.

5. The method of claim 1, wherein the implant surface has an average roughness of 4.0 μm±2 μm.

6. The method of claim 1, wherein the implant surface has a skewness value ranging from 0 to 0.4.

7. The method of claim 1, wherein the mold comprises one or more polymers or copolymers.

8. The method of claim 1, wherein the implant is a breast implant.

9. A method of manufacturing, the method comprising:
applying a biocompatible material to a mold surface of a mold to form a shell of a medical implant, wherein the mold surface is prepared by sandblasting the mold surface with a plurality of abrasive particles, wherein an implant surface of the implant in contact with the mold surface, the implant surface having an average roughness of 4.0 μm±2 μm, a skewness value of 0±0.4, and a plurality of peaks having a height of 15 μm±5 μm;
removing the shell from the mold;
inverting the shell so that the implant surface is an outermost surface of the implant; and
filling the shell with a silicone gel so that the silicone gel covers an inner surface of the shell;
wherein the medical implant is configured for uniform radial compression, such that the medical implant withstands elongation and compacting forces during minimally-invasive surgery without separation of the silicone gel from an inner surface of the shell.

10. The method of claim 9, wherein the implant surface has a kurtosis value ranging from 3.5 to 5.

11. The method of claim 9, wherein the implant surface has a plurality of valleys with a depth of 15 μm±5 μm.

12. The method of claim 9, wherein the mold surface has a uniform surface texture, such that the implant surface has a plurality of peaks and a plurality of valleys evenly distributed across the implant surface.

13. The method of claim 9, wherein the mold comprises one or more polymers or copolymers, and the plurality of abrasive particles comprise sand.

14. A method of manufacturing, the method comprising:
applying a biocompatible material to a mold surface of a mold to form a shell of a medical implant, wherein the mold surface has a uniform surface texture prepared by sandblasting the mold surface with a plurality of abrasive particles, a first surface of the shell being in contact with the mold surface;
wherein the first surface of the shell has an average roughness of 4.0 μm±2 μm, a positive skewness value, an even distribution of peaks having a height of 15 μm±5 μm, and an even distribution of valleys having a depth of 15 μm±5 μm.

15. The method of claim 14, further comprising:
removing the shell from the mold; and
inverting the shell, the first surface of the shell being a mirror image of the mold surface and defining an outermost surface of the medical implant.

16. The method of claim 14, wherein the first surface of the shell has a kurtosis value ranging from 3.5 to 5.

17. The method of claim 14, wherein the first surface of the shell has a kurtosis value ranging from 4 to 7.

18. The method of claim 14, further comprising introducing a silicone gel into a cavity defined by the shell to contact a second surface of the shell opposite the first surface, wherein the medical implant is a breast implant configured for uniform radial compression, such that the breast implant withstands elongation and compacting forces during minimally-invasive surgery without separation of the silicone gel from the second surface.

19. The method of claim 18, wherein the second surface of the shell has an average roughness higher than the average roughness of the first surface of the shell.

20. The method of claim 14, wherein applying the biocompatible material to the mold surface includes applying a first silicone dispersion to the mold, followed by applying a second silicone dispersion over the first silicone dispersion, wherein a chemical composition of the second silicone dispersion is different than a chemical composition of the first silicone dispersion, and wherein at least one of the first silicone dispersion or the second silicone dispersion comprises a pigment to form a colored layer of the shell, the colored layer being a barrier layer.

* * * * *